(12) United States Patent
Nakabayashi et al.

(10) Patent No.: US 6,207,751 B1
(45) Date of Patent: Mar. 27, 2001

(54) SEMICARBAZIDE DERIVATIVE AND A COATING COMPOSITION CONTAINING THE SAME

(76) Inventors: Akira Nakabayashi, Asahikasei-Kamiooka-shataku 1-302, 3-1-1, Ookubo, Kounan-ku, Yokohama-shi, Kanagawa 233 (JP); Tetsuya Murakami, Asahikasei-shataku 511, 181, Kamiodanaka, Nakahara-ku, Kawasaki-shi, Kanagawa 211 (JP)

( * ) Notice: Subject to any disclaimer, the term of this patent is extended or adjusted under 35 U.S.C. 154(b) by 0 days.

(21) Appl. No.: 09/257,365

(22) Filed: Feb. 25, 1999

Related U.S. Application Data

(62) Division of application No. 08/776,127, filed on Dec. 23, 1996, now Pat. No. 5,880,312.

(30) Foreign Application Priority Data

Jul. 4, 1994 (JP) .................................................. 6-151889

(51) Int. Cl.[7] ...................................................... C08F 8/32
(52) U.S. Cl. ........................... 525/61; 524/547; 524/557; 524/560; 524/561; 524/562; 524/589; 524/591; 525/328.5; 525/329.9; 525/330.5; 525/375; 525/376; 525/454; 525/457; 526/85
(58) Field of Search .............................. 525/61, 375, 376, 525/454, 457; 524/547, 557, 560, 561, 562, 589, 591; 536/85

(56) References Cited

U.S. PATENT DOCUMENTS

| | | |
|---|---|---|
| 3,793,238 | 2/1974 | Winkelmann et al. |
| 3,904,796 * | 9/1975 | Zorn et al. ............................ 427/390 |
| 3,998,794 | 12/1976 | Müller et al. |
| 4,240,942 | 12/1980 | Wenzel et al. |
| 4,267,091 | 5/1981 | Geelhaar et al. |
| 4,540,633 | 9/1985 | Kucera et al. |
| 4,590,254 | 5/1986 | Chang et al. |
| 4,983,662 | 1/1991 | Overbeek et al. |
| 5,112,931 * | 5/1992 | Potter et al. ......................... 560/330 |
| 5,141,983 | 8/1992 | Hasegawa et al. |
| 5,504,178 | 4/1996 | Shaffer et al. |

FOREIGN PATENT DOCUMENTS

| | | |
|---|---|---|
| 3632531 | 4/1988 | (DE) . |
| 51-79197 | 7/1976 | (JP) . |
| 57-3850 | 1/1982 | (JP) . |
| 58-3857 | 1/1983 | (JP) . |
| 58-96643 | 6/1983 | (JP) . |
| 4-249587 | 9/1992 | (JP) . |
| 6-16966 | 1/1994 | (JP) . |
| 6-93077 | 5/1994 | (JP) . |
| 6-271761 | 9/1994 | (JP) . |

* cited by examiner

*Primary Examiner*—Bernard Lipman
(74) *Attorney, Agent, or Firm*—Pennie & Edmonds LLP

(57) ABSTRACT

Disclosed is a semicarbazide derivative represented by formula (1) or a terminal-blocked form thereof:

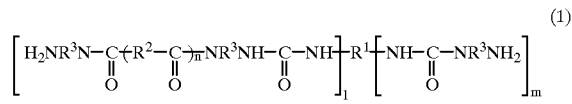

wherein $R^1$ represents a terminal isocyanate group-free polyisocyanate residue or a terminal isocyanate group-free triisocyanate residue; $R^2$ represents an alkylene group, a cycloalkylene group, or an arylene group; each $R^3$ independently represents a hydrogen atom or an alkyl group; n is zero or 1; and each of and m is independently zero or a positive integer, provided l that l and m satisfy the relationship $3 \leq (l+m) \leq 20$. Also disclosed is (δ) a composition comprising (α) at least one member selected from the group consisting of the semicarbazide derivative and a terminal-blocked form thereof and (β) at least one member selected from the group consisting of a hydrophilic group-containing compound and a terminal-blocked form thereof. Also disclosed is a coating composition comprising (γ) a polycarbonyl compound, and component (α) or composition (δ) as a curing agent therefor. The coating composition of the present invention has not only excellent cold-curing ability and storage stability, but is also capable of forming, at relatively low temperatures, a coating which has excellent properties, such as excellent water resistance, stain resistance, hardness and the like.

20 Claims, 10 Drawing Sheets

SEMICARBAZIDE DERIVATIVE AND A COATING COMPOSITION CONTAINING THE SAME

This is a division of application Ser. No. 08/776,127 filed Dec. 23, 1996 which is now U.S. Pat. No. 5,880,312.

BACKGROUND OF THE INVENTION

1. Technical Field

The present invention relates to a semicarbazide derivative and a coating composition containing the same and a polycarbonyl compound. More particularly, the present invention is concerned with a semicarbazide derivative or a terminal-blocked form thereof, which is obtained by reacting a polyisocyanate having from 3 to 20 isocyanate groups in a molecule thereof with hydrazine or a derivative thereof, or a mixture of non-terminal-blocked and terminal-blocked forms of hydrazine or a derivative thereof. The present invention is also concerned with a coating composition comprising at least one member selected from the semicarbazide derivative and a terminal-blocked form thereof as a curing agent, and a polycarbonyl compound. Further, the present invention is also concerned with a composition comprising at least one member selected from the semicarbazide derivative and a terminal-blocked form thereof and at least one member selected from a hydrophilic group-containing compound and a terminal-blocked form thereof (this composition is hereinafter frequently referred to as "semicarbazide composition"), and further concerned with a coating composition comprising this semicarbazide composition and a polycarbonyl compound.

The coating composition of the present invention has not only excellent cold-curing ability and storage stability, but is also capable of forming a coating which has excellent properties, such as excellent water resistance, stain resistance, hardness, toughness, weatherability, dispersion characteristics of pigment, gloss retentivity, adhesion properties, rust preventive properties, water impermeability, heat resistance and chemical resistance, and which is extremely excellent especially in water resistance, stain resistance and hardness. Therefore, the coating composition of the present invention can be advantageously used as a paint, an undercoating or finish coating material for building materials, an adhesive, a pressure-sensitive adhesive, a processing agent for papers, or a finish coating material for textile fabrics.

2. Prior Art

In recent years, in the field of coatings, an aqueous emulsion has been drawing attention as a substitute material useful in the shift from organic-solvent type coating materials to aqueous-solvent type coating materials. However, coatings formed from conventional aqueous emulsion type coating materials are unsatisfactory in respect of various properties, such as water resistance, stain resistance and hardness, as compared to coatings formed from organic-solvent type coating materials.

In an attempt to improve the above-mentioned properties of coatings formed from aqueous emulsion type coating materials, it has generally been conventional practiced to introduce a functional group into an aqueous emulsion type coating material so that a coating comprised of a cross-linked polymer (hereinafter frequently referred to as "cross-linked coating") can be formed.

With respect to an aqueous emulsion type coating material which is capable of forming a cross-linked coating, from the viewpoint of ease in coating operation and the like, it has been desired that such a coating material be of a cold-curing, one-pack type such that a coating material comprising a polymer and a curing agent therefor, both dispersed in an aqueous medium can be cured even without heating to form a cured film due to the evaporation of the aqueous medium after the coating. In recent years, as a coating material satisfying the above desire, a hydrazone-crosslinking type aqueous emulsion obtained by the dehydration-condensation reaction between a carbonyl group and a hydrazide group has been attracting attention.

For example, in Examined Japanese Patent Application Publication No. 46-20053, Unexamined Japanese Patent Application Laid-Open Specification No. 57-3850, Unexamined Japanese Patent Application Laid-Open Specification No. 57-3857, Unexamined Japanese Patent Application Laid-Open Specification No. 58-96643 and Unexamined Japanese Patent Application Laid-Open Specification No. 4-249587, it is proposed to add a dicarboxylic acid bishydrazide as a curing agent to an aqueous dispersion of a carbonyl group-containing copolymer, to thereby obtain a coating composition which has not only good cold-curing ability and storage stability, but is also capable of forming a coating which has excellent hardness and stain resistance. However, with respect to this proposal, the above-mentioned dicarboxylic acid bishydrazide used as a curing agent undergoes hydrolysis during the storage of the coating composition containing the same, so that the cross-linking ability (i.e., curing ability) of the coating composition is lowered with the lapse of time and, hence, the ability of the coating composition to form a coating having good hardness, stain resistance, solvent resistance and the like is lowered with time. In addition, this proposal has a problem in that, because of the use of a dicarboxylic acid bishydrazide (such as adipic acid bishydrazide) having a low compatibility with a carbonyl group-containing copolymer and having a high hydrophilicity, the obtained cross-linked coating is inevitably caused to have extremely poor water resistance.

As can be seen from the above, aqueous coating compositions containing a conventional curing agent and a carbonyl compound become lowered in curing properties with time, so that when such a coating composition is applied to the surface of a substrate, the composition cannot exhibit a satisfactory curing ability. Further, since a conventional coating composition employs, as a curing agent, a dicarboxylic acid bishydrazide having a low compatibility with a polycarbonyl compound, the conventional coating composition has problems in that a cross-linked coating formed therefrom has extremely low water resistance. Therefore, it has been desired to develop an aqueous coating composition which has not only an excellent cold-curing ability and storage stability, but is also capable of forming a coating which has excellent properties, particularly excellent water resistance, stain resistance and hardness.

SUMMARY OF THE INVENTION

The present inventors have made extensive and intensive studies with a view toward solving the above-mentioned problems accompanying the prior art. As a result, it has unexpectedly been found that each of (α) at least one member selected from the group consisting of a semicarbazide derivative and a terminal-blocked form thereof which are obtained by reacting a polyisocyanate having from 3 to 20 isocyanate groups (hereinafter frequently referred to as "NCO groups") with hydrazine or a derivative thereof, or a mixture of non-terminal-blocked or terminal-blocked forms of hydrazine or a hydrazine derivative, and (δ) a semicarbazide composition comprising at least one member selected from the group consisting of the semicarbazide derivative and a terminal-blocked form thereof and at least one member selected from the group consisting of a hydrophilic group-containing compound and a terminal-blocked form thereof, exhibits extremely high compatibility with a polycarbonyl compound. Further, the present inventors have also unexpectedly found that when (α) at least one member selected from the group consisting of the semicarbazide derivative and a terminal-blocked form thereof or (δ) a semicarbazide composition comprising at least one member selected from the group consisting of the semicarbazide derivative and a terminal-blocked form thereof and at least one member selected from the group consisting of a hydrophilic group-containing compound and a terminal-blocked form thereof, is combined as a curing agent with a polycarbonyl compound to prepare an aqueous coating composition, the aqueous coating composition has not only excellent cold-curing ability and storage stability, but is also capable of forming, at relatively low temperatures (ambient temperature), a coating having an extremely high cross-linking degree and having various excellent properties including excellent hardness, toughness, water resistance and stain resistance, the coating being comparable to a coating obtained from a conventional organic solvent type coating material, especially in water resistance. The present invention has been completed, based on the above findings.

Accordingly, it is an object of the present invention to provide a novel compound which exhibits extremely high compatibility with a polycarbonyl compound and is extremely useful as a curing agent for a polycarbonyl compound.

It is another object of the present invention to provide a coating composition comprising the above novel compound and a polycarbonyl compound, which coating composition has not only excellent cold-curing ability and storage stability, but is also capable of forming, at relatively low temperatures, a coating having excellent properties, such as an excellent water resistance, stain resistance, hardness, toughness, weatherability, dispersion characteristics of pigment, gloss retentivity, adhesion properties, rust preventive properties, water impermeability, heat resistance and chemical resistance (e.g. solvent resistance) (the coating is extremely excellent especially in water resistance, stain resistance, hardness and toughness).

The foregoing and other objects, features and advantages of the present invention will be apparent from the following detailed description and claims, taken in connection with the accompanying drawings.

DETAILED DESCRIPTION OF THE INVENTION

Figure 1:
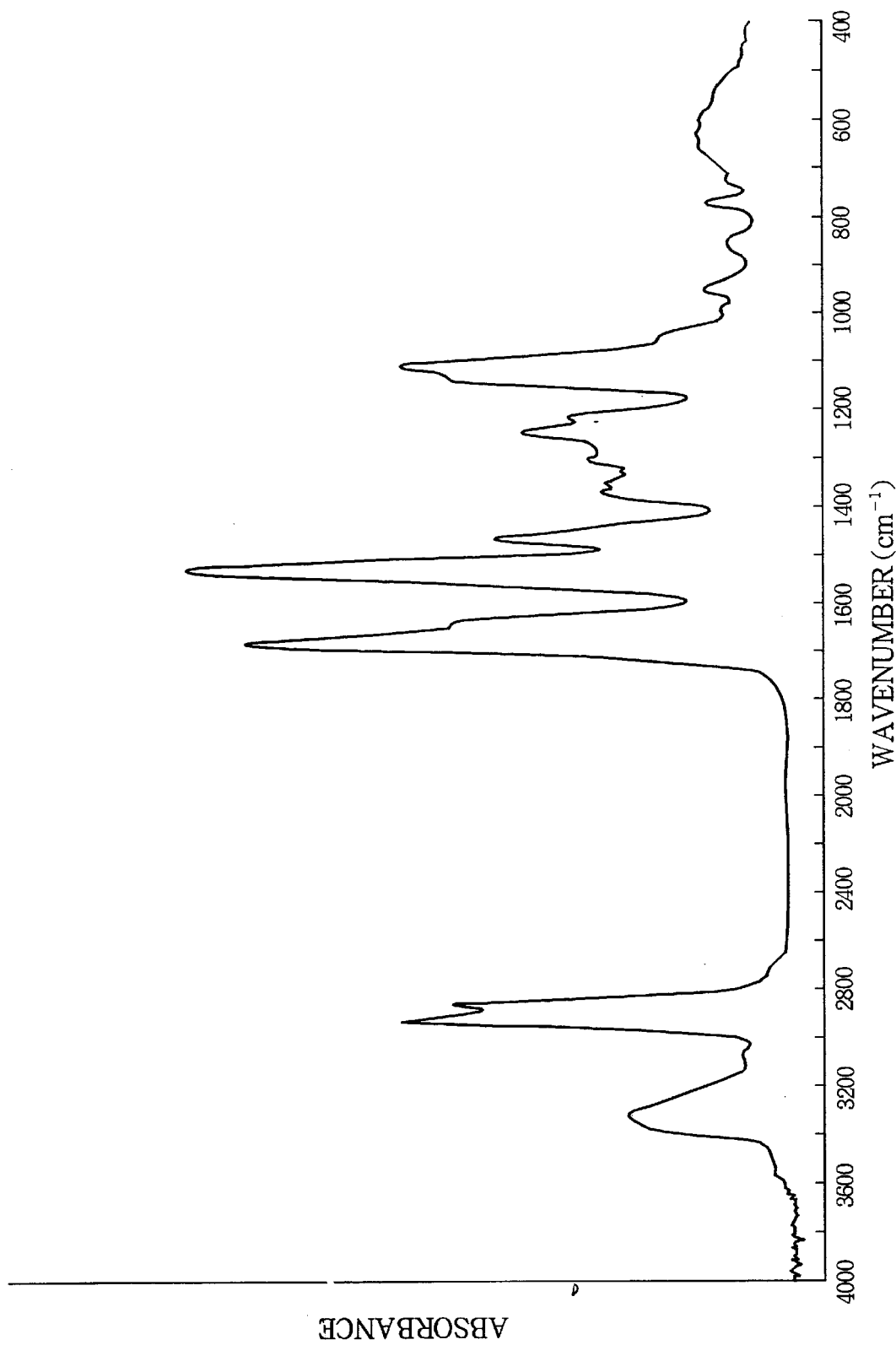
FIG. 1 shows an infrared absorption spectrum of the semicarbazide composition obtained in Example 1.

In one aspect of the present invention, there is provided a semicarbazide derivative represented by formula (1) or a terminal-blocked form thereof:

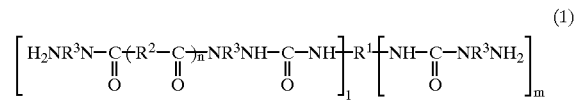

(1)

wherein $R^1$ represents a terminal isocyanate group-free polyisocyanate residue derived from a 3- to 20-mer oligomer of at least one diisocyanate selected from the group consisting of a linear or branched $C_2$–$C_{20}$ alkylene diisocyanate, a $C_5$–$C_{20}$ cycloalkylene diisocyanate which is unsubstituted or substituted with a $C_1$–$C_{18}$ alkyl group, a $C_1$–$C_8$ alkoxy group or a $C_1$–$C_6$ alkylene group, a $C_6$–$C_{20}$ arylene diisocyanate which is unsubstituted or substituted with a $C_1$–$C_{18}$ alkyl group or a $C_1$–$C_8$ alkoxy group, and a $C_8$–$C_{20}$ aralkylene diisocyanate which is unsubstituted or substituted with a $C_1$–$C_{18}$ alkyl group or a $C_1$–$C_8$ alkoxy group, or $R^1$ represents a terminal isocyanate group-free. triisocyanate residue derived from a $C_2$–$C_{20}$ alkylene diisocyanate substituted with a $C_1$–$C_8$ isocyanatoalkyl group;

$R^2$ represents a linear or branched $C_2$–$C_{20}$ alkylene group, a $C_5$–$C_{20}$ cycloalkylene group, or a $C_6$–$C_{10}$ arylene group which is unsubstituted or substituted with a $C_1$–$C_{18}$ alkyl group or a $C_1$–$C_8$ alkoxy group;

each $R^3$ independently represents a hydrogen atom or a $C_1$–$C_{20}$ alkyl group;

n is zero or 1; and each of l and m is independently zero or a positive integer, provided that l and m satisfy the relationship $3 \leq (l+m) \leq 20$, wherein the terminal-blocked form of the semicarbazide derivative represented by formula (1) has at least one blocked terminal group derived from the terminal group $H_2NR^3N$— in formula (1), the blocked terminal group being represented by the formula $R^9R^8C=NR^3N$—, wherein each of $R^8$ and $R^9$ independently represents a hydrogen atom, a linear or branched $C_1$–$C_{20}$ alkyl group, a $C_5$–$C_{20}$ cycloalkyl group, or a $C_6$–$C_{10}$ aryl group which is unsubstituted or substituted with a $C_1$–$C_{18}$ alkyl group or a $C_1$–$C_8$ alkoxy group, with the proviso that the $R^8$ and $R^9$ together optionally form a ring structure.

In another aspect of the present invention, there is is provided a composition comprising (α) at least one member selected from the group consisting of the semicarbazide derivative and terminal-blocked form thereof according to claim 1, and (β) at least one member selected from the group consisting of a hydrophilic group-containing compound represented by formula (7) and a terminal-blocked form thereof:

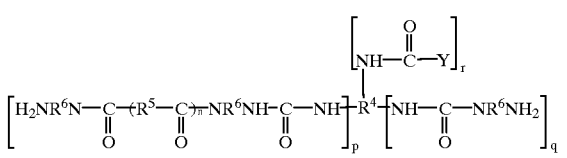
(7)

wherein R⁴ represents a terminal isocyanate group-free polyisocyanate residue derived from a 3- to 20-mer oligomer of at least one diisocyanate selected from the group consisting of a linear or branched $C_2$–$C_{20}$ alkylene diisocyanate, a $C_5$–$C_{20}$ cycloalkylene diisocyanate which is unsubstituted or substituted with a $C_1$–$CI_8$ alkyl group, a $C_1$–$C_8$ alkoxy group or a $C_1$–$C_6$ alkylene group, a $C_6$–$C_{20}$ arylene diisocyanate which is unsubstituted or substituted with a $C_1$–$C_{18}$ alkyl group or a $C_1$–$C_8$ alkoxy group, and a $C_8$–$C_{20}$ aralkylene diisocyanate which is unsubstituted or substituted with a $C_1$–$C_{18}$ alkyl group or a $C_1$–$C_8$ alkoxy group, or R⁴ represents a terminal isocyanate group-free diisocyanate residue derived from the diisocyanate, or R⁴ represents a terminal isocyanate group-free triisocyanate residue derived from a $C_2$–$C_{20}$ alkylene diisocyanate substituted with a $C_1$–$C_8$ isocyanatoalkyl group;

R⁵ represents a linear or branched $C_2$–$C_{20}$ alkylene group, a $C_5$–$C_{20}$ cycloalkylene group, or a $C_6$–$C_{10}$ arylene group which is unsubstituted or substituted with a $C_1$–$C_{18}$ alkyl group or a $C_1$–$C_8$ alkoxy group;

each R⁶ independently represents a hydrogen atom or a $C_1$–$C_{20}$ alkyl group;

Y represents an organic group having at least one group selected from the group consisting of a nonionic hydrophilic group, an ionic hydrophilic group and a group which is capable of being converted into an ionic hydrophilic group;

n is zero or 1; and each of p and q is independently zero or a positive integer, and r is a positive integer, provided that p and q satisfy the relationship (p+q)≧0, and p, q and r satisfy the relationship 2≦(p+q+r)≦20, wherein the terminal-blocked form of the compound represented by formula (7) has at least one blocked terminal group derived from the terminal group H₂NR⁶N— in formula (7), the blocked terminal group being represented by the formula R⁹R⁸C=NR⁶N—, wherein each of R⁸ and R⁹ independently represents a hydrogen atom, a linear or branched $C_1$–$C_{20}$ alkyl group, a $C_5$–$C_{20}$ cycloalkyl group, or a $C_6$–$C_{10}$ aryl group which is unsubstituted or substituted with a $C_1$–$C_{18}$ alkyl group or a $C_1$–$C8$ alkoxy group, with the proviso that the R⁸ and R⁹ together optionally form a ring structure, and wherein the weight ratio of the component (α) to the component (β) is 10/90 to 99/1.

In still another aspect of the present invention, there is provided a coating composition comprising (α) at least one member selected from the group consisting of the semicarbazide derivative and terminal-blocked form thereof according to claim 1, and (γ) a polycarbonyl compound selected from the group consisting of a carbonyl group-containing polyurethane, an acetoacetylated polyvinyl alcohol, an acetoacetylated hydroxyalkyl cellulose, and a carbonyl group-containing copolymer of 0.1 to 30% by weight of (a) a carbonyl group-containing ethylenically unsaturated monomer with 70 to 99.9% by weight of (b) an ethylenically unsaturated monomer copolymerizable with the monomer (a).

In a further aspect of the present invention, there is provided a coating composition comprising (δ) the composition according to claim 7, and (γ) a polycarbonyl compound selected from the group consisting of a carbonyl group-containing polyurethane, an acetoacetylated polyvinyl alcohol, an acetoacetylated hydroxyalkyl cellulose, and a carbonyl group-containing copolymer of 0.1 to 30% by weight of (a) a carbonyl group-containing ethylenically unsaturated monomer with 70 to 90% by weight of (b) an ethylenically unsaturated monomer copolymerizable with the monomer (a).

In the present invention, each of alkyl groups and each alkyl moiety of alkoxy groups, which are mentioned as substituents of various groups represented by R¹–R¹¹, A₁–A³, and X¹–X³ which are mentioned above and/or below may be in a straight chain or branched form.

The semicarbazide derivative of the present invention can be obtained by reacting a polyisocyanate having from 3 to 20 NCO groups in a molecule thereof with hydrazine or a derivative thereof.

By contrast, with respect to a semicarbazide derivative obtained by reacting a polyisocyanate having two NCO groups in a molecule thereof with hydrazine or a derivative thereof, a coating composition containing such a semicarbazide derivative as a curing agent is low in cross-linking ability, so that a coating having not only excellent toughness but also excellent water resistance cannot be obtained.

As polyisocyanates having 3 to 20 NCO groups in a molecule thereof, there can be mentioned, for example, a polyisocyanate obtained by oligomerizing a diisocyanate into a 3- to 20-mer oligomer while forming a biuret linkage, a urea linkage, an isocyanurate linkage, a urethane linkage, an allophanate linkage, a uretodione linkage or the like. With respect to the method for producing the polyisocyanate and to these linkages in the polyisocyanate, reference can be made to, for example, "Polyurethane Handbook" edited by G. Oertel (published in 1985 by Hanser Publishers, Germany).

The diisocyanate which can be used for producing the semicarbazide derivative of the present invention represented by formula (1) is at least one diisocyanate selected from the group consisting of a linear or branched $C_2$–$C_{20}$ alkylene diisocyanate, a $C_5$–$C_{20}$ cycloalkylene diisocyanate which is unsubstituted or substituted with a $C_1$–$C_{18}$ alkyl group, a $C_1$–$C_8$ alkoxy group or a $C_1$–$C_6$ alkylene group, a $C_6$–$C_{20}$ arylene diisocyanate which is unsubstituted or substituted with a $C_1$–$C_{18}$ alkyl group or a $C_1$–$C_8$ alkoxy group, and a $C_8$–$C_{20}$ aralkylene diisocyanate which is unsubstituted or substituted with a $C_1$–$C_{18}$ alkyl group or a $C_1$–$C_8$ alkoxy group.

Examples of the above-mentioned diisocyanates include alkylene diisocyanates, such as hexamethylene diisocyanate (HDI); cycloalkylene diisocyanates, such as 4,4'-methylenebiscyclohexyl diisocyanate (hydrogenated MDI), isophorone diisocyanate (IPDI) and dimethylcyclohexane diisocyanate (hydrogenated XDI); arylene diisocyanates, such as 2,4-tolylene diisocyanate, 2,6-tolylene diisocyanate and a mixture thereof (TDIs), diphenylmethane-4,4'-diisocyanate (MDI), naphthalene-1,5-diisocyanate (NDI), 3,3-dimethyl-4,4-biphenylene diisocyanate (TODI), crude TDIs, polymethylene polyphenyldiisocyanate, crude MDI and phenylene diisocyanate; and aralkylene diisocyanates, such as xylylene diisocyanate (XDI). These diisocyanates are used individually or in combination.

Among the above-mentioned diisocyanates, from the viewpoint of improving the weatherability and thermal-yellowing resistance of a coating obtained from the coating composition containing the semicarbazide derivative (which can be obtained by using such a diisocyanate) as a curing agent and a polycarbonyl compound, alkylene diisocyanates and cycloalkylene diisocyanates are preferred.

As mentioned above, a polyisocyanate which is a 3- to 20-mer oligomer of at least one diisocyanate selected from these diisocyanates is reacted with hydrazine or a derivative thereof, to thereby obtain the semicarbazide derivative of the present invention. In this case, $R^1$ in formula (1) represents a terminal isocyanate group-free polyisocyanate residue.

In addition to the semicarbazide derivative produced from the above-mentioned polyisocyanate, the semicarbazide derivative of the present invention can also be one which is obtained by reacting a $C_2$–$C_{20}$ alkylene diisocyanate substituted with a $C_1$–$C_8$ isocyanatoalkyl group, such as 1,8-diisocyanato-4-isocyanatomethyloctane, with hydrazine or a derivative thereof. In this case, $R^1$ in formula (1) represents a terminal isocyanate group-free triisocyanate residue derived from the above-mentioned alkylene diisocyanate substituted with an isocyanatoalkyl group.

In the present invention, from the viewpoint of the desired compatibility with a polycarbonyl compound, it is preferred to use a polyisocyanate having 3 to 20 NCO groups in a molecule thereof which is obtained by oligomerizing a diisocyanate.

In the present invention, the semicarbazide derivative obtained by reacting the above-mentioned polyisocyanate with hydrazine or a derivative thereof is multifunctional. Therefore, a coating composition comprising the above semicarbazide derivative as a curing agent has high cross-linking ability and is hence capable of forming a tough coating. When the number of NCO groups contained in the polyisocyanate exceeds 20 per molecule, the number of formed semicarbazide groups [herein, for convenience, sake, a group represented by the formula

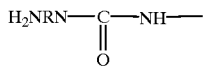

(wherein R represents a linear or branched $C_2$–$C_{20}$ alkylene group, a $C_5$–$C_{20}$ cycloalkylene group, or a $C_6$–$C_{10}$ arylene group which is unsubstituted or substituted with a $C_6$–$C_{18}$ alkyl group or a $C_1$–$C_8$ alkoxy group) is frequently referred to as "semicarbazide group"] becomes too large, so that the semicarbazide derivative exhibits high viscosity, making it difficult to handle the semicarbazide derivative. For this reason, the polyisocyanate to be used in the present invention contains 3 to 20 NCO groups, preferably 3 to 10 NCO groups.

Of these polyisocyanates, preferable examples include a polyisocyanate having an isocyanurate linkage (isocyanurate type polyisocyanate), which is obtained by a method in which a diisocyanate is subjected to a cyclotrimerization reaction in the presence of a catalyst, and the reaction is terminated when the conversion has reached a value within the range of from about 5 to about 80% by weight, preferably from about 10 to about 60% by weight, followed by removal of the excess diisocyanate for purification of the resultant product. Illustrative examples of isocyanurate type polyisocyanates include those which are derived from hexamethylene diisocyanate, as disclosed in Unexamined Japanese Patent Application Laid-Open Specification No. 55-38380; those which are obtained by copolymerizing isophorone diisocyanate and hexamethylene diisocyanate, as disclosed in Unexamined Japanese Patent Application Laid-Open Specification No. 57-78460; multi-functional alcohol-modified polyisocyanates as disclosed in Unexamined Japanese Patent Application Laid-Open Specification No. 57-47321; low viscosity polyisocyanates as disclosed in Unexamined Japanese Patent Application Laid-Open Specification No. 64-33115; highly branched polyisocyanates as disclosed in Japanese Patent Application No. 6-16688; and the like.

In the present invention, is a semicarbazide derivative or a terminal-blocked form thereof, which is obtained by reacting the above-mentioned isocyanurate type polyisocyanate with a non-terminal-blocked or terminal-blocked form of hydrazine or of a hydrazine derivative, a semicarbazide derivative or a terminal blocked form thereof, wherein the polyisocyanate residue represented by $R^1$ has a structure comprising at least a 3-mer skelton among skeltons of the 3- to 20-mer oligomers of the at least one diisocyanate, the 3-mer skelton being represented by the following formula (2') is preferable (with respect to hydrazine or a derivative thereof in a terminal-blocked form and to the semicarbazide derivative in a terminal-blocked form, explanation is made hereinbelow):

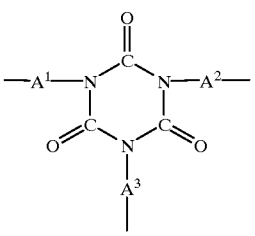

(2')

wherein each of $A^1$, $A^2$ and $A^3$ independently represents a linear or branched $C_2$–$C_{20}$ alkylene group, a $C_5$–$C_{20}$ cycloalkylene group which is unsubstituted or substituted with a $C_1$–$C_{18}$ alkyl group, a $C_1$–$C_8$ alkoxy group or a $C_1$–$C_6$ alkylene group, a $C_6$–$C_{20}$ arylene group which is unsubstituted or substituted with a $C_1$–$C_{18}$ alkyl group or a $C_1$–$C_8$ alkoxy group, or a $C_8$–$C_{20}$ aralkylene group which is unsubstituted or substituted with a $C_1$–$C_{18}$ alkyl group or a $C_1$–$C_8$ alkoxy group.

For example, the 3-mer oligomer of a diisocyanate, which is formed by isocyanurate bonding, is represented by the following formula (2):

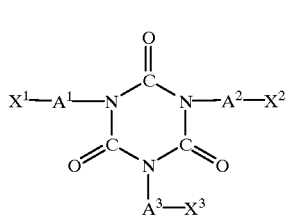

(2)

wherein each of $A^1$, $A^2$ and $A^3$ is as defined for formula (2') above; and each of $X^1$, $X^2$ and $X^3$ independently represents a group represented by formula (3) or (4):

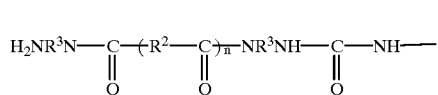
(3)

wherein $R^2$ represents a linear or branched $C_2$–$C_{20}$ alkylene group, a $C_5$–$C_{20}$ cycloalkylene group, or a $C_6$–$C_{10}$ arylene group which is unsubstituted or substituted with a $C_1$–$C_{18}$ alkyl group or a $C_1$–$C_8$ alkoxy group; each $R^3$ independently represents a hydrogen atom or a $C_1$–$C_{20}$ alkyl group; and n is zero or 1,

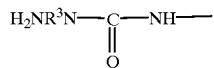
(4)

wherein $R^3$ is as defined above.

The terminal-blocked form of the semicarbazide derivative represented by formula (2) has at least one blocked terminal group derived from the terminal group $H_2NR^3N$— in formula (3) or (4), which blocked terminal group is represented by the formula $R^9R^8C{=}NR^3N$—, wherein each of $R^8$ and $R^9$ independently represents a hydrogen atom, a linear or branched $C_1$–$C_{20}$ alkyl group, a $C_5$–$C_{20}$ cycloalkyl group, or a $C_6$–$C_{10}$ aryl group which is unsubstituted or substituted with a $C_1$–$C_{18}$ alkyl group or a $C_1$–$C_8$ alkoxy group, with the proviso that the $R^8$ and $R^9$ together optionally form a ring structure.

Other preferred examples of polyisocyanates include those which have a biuret linkage (biuret type polyisocyanate). These biuret type polyisocyanates are obtained by reacting a biuretizing agent, such as water, t-butanol, urea or the like, with a diisocyanate in a molar ratio of the biuretizing agent to the diisocyanate in the range of from about ½ to about ¹⁄₁₀₀, preferably from about ⅓ to about ¹⁄₅₀, followed by removing the excess diisocyanate for purification. Illustrative examples of biuret type polyisocyanates include those which are derived from hexamethylene diisocyanate, as disclosed in Unexamined Japanese Patent Application Laid-Open Specification No. 53-106797 and Unexamined Japanese Patent Application Laid-Open Specification No. 55-11452; those which are obtained by copolymerizing isophorone diisocyanate and hexamethylene diisocyanate, as disclosed in Unexamined Japanese Patent Application Laid-Open Specification No. 59-95259; and the like.

In the present invention, as semicarbazide derivative or a terminal-blocked form thereof, which is obtained by reacting the above-mentioned biuret type polyisocyanate with a non-terminal-blocked or terminal-blocked form of hydrazine or of a hydrazine derivative, a semicarbazide derivative or a terminal blocked form thereof, wherein the polyisocyanate residue represented by $R^1$ has a structure comprising at least a 3-mer skelton among skeltons of the 3- to 20-mer oligomers of the at least one diisocyanate, the 3-mer skelton being represented by the following formula (2') is also preferable:

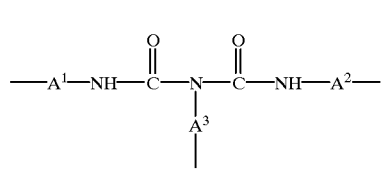
(5')

wherein each of $A^1$, $A^2$ and $A^3$ independently represents a linear or branched $C_2$–$C_{20}$ alkylene group, a $C_5$–$C_{20}$ cycloalkylene group which is unsubstituted or substituted with a $C_1$–$C_{18}$ alkyl group, a $C_1$–$C_8$ alkoxy group or a $C_1$–$C_6$ alkylene group, a $C_6$–$C_{20}$ arylene group which is unsubstituted or substituted with a $C_1$–$C_{18}$ alkyl group or a $C_1$–$C_8$ alkoxy group, or a $C_8$–$C_{20}$ aralkylene group which is unsubstituted or substituted with a $C_1$–$C_{18}$ alkyl group or a $C_1$–$C_8$ alkoxy group.

For example, the 3-mer oligomer of a diisocyanate, which is formed by biuret bonding, is represented by the following formula (5):

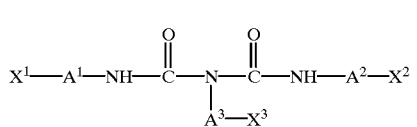
(5)

wherein each of $A^1$, $A^2$ and $A^3$ is as defined for formula (5') above; and each of $X^1$, $X^2$ and $X^3$ independently represents a group represented by formula (3) or (4):

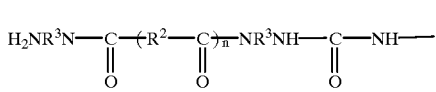
(3)

wherein $R^2$ represents a linear or branched $C_2$–$C_{20}$ alkylene group, a $C_5$–$C_{20}$ cycloalkylene group, or a $C_6$–$C_{10}$ arylene group which is unsubstituted or substituted with a $C_1$–$C_{18}$ alkyl group or a $C_1$–$C_8$ alkoxy group; each $R^3$ independently represents a hydrogen or a $C^1$–$C^{20}$ alkyl group; and n is zero or 1,

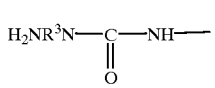
(4)

wherein $R^3$ is as defined above.

The terminal-blocked form of the semicarbazide derivative represented by formula (5) has at least one blocked terminal group derived from the terminal group $H_2NR^3N$— in formula (3) or (4), which blocked terminal group is represented by the formula $R^9R^8C{=}NR^3N$—, wherein each of $R^8$ and $R^9$ independently represents a hydrogen atom, a linear or branched $C_1$–$C_{20}$ alkyl group, a $C_5$–$C_{20}$ cycloalkyl group, or a $C_6$–$C_{10}$ aryl group which is unsubstituted or substituted with a $C_1$–$C_{18}$ alkyl group or a $C_1$–$C_8$ alkoxy group, with the proviso that the $R^8$ and $R^9$ together optionally form a ring structure.

A semicarbazide derivative or a terminal-blocked form thereof which is obtained by using the above-mentioned isocyanurate type polyisocyanate or the above-mentioned biuret type polyisocyanate, has excellent compatibility with a polycarbonyl compound, and hence by applying to the surface of a substrate a coating composition comprising a polycarbonyl compound and at least one member selected from the group consisting of the semicarbazide derivative and a terminal-blocked form thereof as a curing agent for the polycarbonyl compound, a coating having excellent hardness, water resistance, chemical resistance, weatherability, heat resistance, appearance and the like can be obtained.

Further examples of preferred polyisocyanates to be used in the present invention include a polyisocyanate having a urethane linkage (urethane type polyisocyanate), which is obtained by reacting a diisocyanate with a polycaprolactone polyol in a molar ratio of —NCO groups to —OH groups in the range of from about 3 to about 50, preferably from about 5 to about 40, followed by removing the excess diisocyanate for purification.

A semicarbazide derivative or a terminal-blocked form thereof which is obtained by using the above-mentioned urethane type polyisocyanate, has excellent compatibility with a polycarbonyl compound, and hence by applying to the surface of a substrate a coating composition comprising a polycarbonyl compound and at least one member selected from the group consisting of the semicarbazide derivative and a terminal-blocked form thereof as a curing agent for the polycarbonyl compound, a coating having excellent flexibility can be obtained. Especially when the weight average molecular weight of the semicarbazide derivative is less than 2,000, and the weight average molecular weight of the terminal blocked form of the semicarbazide derivative is less than 3,000, a coating having excellent hardness, flexibility, water resistance, heat resistance, and the like can be obtained.

In the present invention, a as semicarbazide derivative or a terminal-blocked form thereof, which is obtained by reacting the above-mentioned urethane type polyisocyanate with a non-terminal-blocked or terminal-blocked form of hydrazine or of a hydrazine derivative, a semicarbazide derivative or a terminal blocked form thereof, wherein the polyisocyanate residue represented by $R^1$ has a structure comprising at least a 3-mer skelton among skeltons of the 3- to 20-mer oligomers of the at least one diisocyanate, the 3-mer skelton being represented by the following formula (2'), is also preferable:

(6')

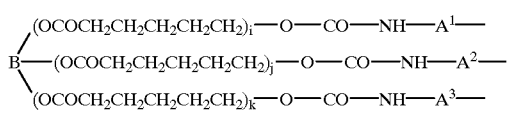

wherein each of $A^1$, $A^2$ and $A^3$ independently represents a linear or branched $C_2$–$C_{20}$ alkylene group, a $C_5$–$C_{20}$ cycloalkylene group which is unsubstituted or substituted with a $C_1$–$C_{18}$ alkyl group, a $C_1$–$C_8$ alkoxy group or a $C_1$–$C_6$ alkylene group, a $C_6$–$C_{20}$ arylene group which is unsubstituted or substituted with a $C_1$–$C_{18}$ alkyl group or a $C_1$–$C_8$ alkoxy group, or a $C_8$–$C_{20}$ aralkylene group which is unsubstituted or substituted with a $C_1$–$C_{18}$ alkyl group or a $C_1$–$C_8$ alkoxy group;

B represents a terminal hydroxyl group-free triol residue derived from a $C_1$–$C_{20}$ aliphatic hydrocarbon triol, a $C_5$–$C_{20}$ alicyclic hydrocarbon triol or a $C_6$–$C_{20}$ aromatic hydrocarbon triol;

each of i, j and k is independently an integer of from 0 to 50, provided that i, j and k satisfy the relationship (i+j+k) ≦1, For example, the 3-mer oligomer of a diisocyanate, which is formed by urethane bonding, is represented by the following formula (6):

(6)

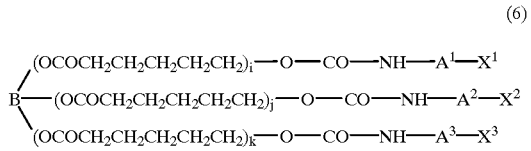

wherein each of $A^1$, $A^2$ and $A^3$ is as defined for formula (6') above; and each of $X^1$, $X^2$ and $X^3$ independently represents a group represented by formula (3) or (4):

(3)

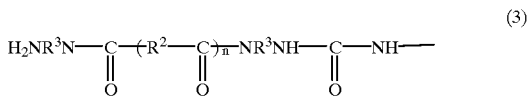

wherein $R^2$ represents a linear or branched $C_2$–$C_{20}$ alkylene group, a $C_5$–$C_{20}$ cycloalkylene group, or a $C_6$–$C_{10}$ arylene group which is unsubstituted or substituted with a $C_1$–$C_{18}$ alkyl group or a $C_1$–$C_8$ alkoxy group; each $R^3$ independently represents a hydrogen atom or a $C_1$–$C_{20}$ alkyl group; and n is zero or 1, (4)

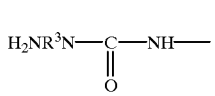

wherein $R^3$ is as defined above.

The terminal-blocked form of the semicarbazide derivative represented by formula (6) has at least one blocked terminal group derived from the terminal group $H_2NR^3N$— in formula (3) or (4), which blocked terminal group is represented by the formula $R^9R^8C=NR^3N$—, wherein each of $R^8$ and $R^9$ independently represents a hydrogen atom, a linear or branched $C_1$–$C_{20}$ alkyl group, a $C_5$–$C_{20}$ cycloalkyl group, or a $C_6$–$C_{10}$ aryl group which is unsubstituted or substituted with a $C_1$–$C_{18}$ alkyl group or a $C_1$–$C_8$ alkoxy group, with the proviso that the $R^8$ and $R^9$ together optionally form a ring structure.

Examples of hydrazine or derivatives thereof to be used in the present invention include hydrazine and a hydrate thereof; monoalkyl-substituted hydrazines, such as monomethyl hydrazine, monoethyl hydrazine and monobutyl hydrazine; dihydrazine compounds, such as ethylene-1,2-dihydrazine, propylene-1,3-dihydrazine and butylene-1,4-dihydrazine; dicarboxylic acid bishydrazides, such as oxalic acid bishydrazide, malonic acid bishydrazide, succinic acid bishydrazide, glutaric acid bishydrazide, adipic acid bishydrazide, sebacic acid bishydrazide, maleic acid bishydrazide, fumaric acid bishydrazide, itaconic acid bishydrazide, isophthalic acid bishydrazide and phthalic acid bishydrazide; tricarboxylic acid trihydrazides, such as trimellitic acid trihydrazide; carbonic acid bishydrazides represented by the following formula (8):

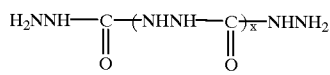

(8)

wherein x is 0 or 1; and
bissemicarbazides represented by the following formula (9):

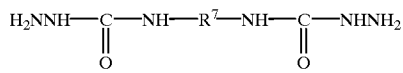

(9)

wherein $R^7$ represents a linear or branched $C_2$–$C_{20}$ alkylene group, a $C_5$–$C_{20}$ cycloalkylene group, or a $C_6$–$C_{10}$ arylene group which is unsubstituted or substituted with a $C_1$–$C_{18}$ alkyl group or a $C_1$–$C_8$ alkoxy group.

Mixtures of hydrazine or derivatives thereof mentioned above can also be used in the present invention.

In the present invention, for the purpose of preventing the semicarbazide derivative from forming a high molecular weight molecule due to a chain extension of hydrazine or derivatives thereof, hydrazine or derivatives thereof can be converted into hydrazone or derivatives thereof by reacting the hydrazine or derivatives thereof with a monoketone (e.g., acetone, methyl ethyl ketone, methyl isobutyl ketone or cyclohexanone) or a monoaldehyde (e.g., acetoaldehyde) to thereby block one terminal group of a part of molecules of the hydrazine or derivatives thereof. The monoketone and monoaldehyde usable in the present invention are represented by the following formula (10):

$$R^8R^9C=O \quad (10)$$

wherein each of $R^8$ and $R^9$ independently represents a hydrogen atom, a linear or branched $C_1$–$C_{20}$ alkyl group, a $C_5$–$C_{20}$ cycloalkyl group, or a $C_6$–$C_{10}$ aryl group which is unsubstituted or substituted with a $C_1$–$C_{18}$ alkyl group or a $C_1$–$C_8$ alkoxy group, with the proviso that the $R^8$ and $R^9$ together optionally form a ring structure.

When the above-mentioned terminal-blocked form of hydrazine or derivatives thereof is used, a terminal-blocked form of the semicarbazide derivative which has at least one terminal semicarbazide group blocked and converted into a semicarbazone group, or a mixture of a semicarbazide derivative and a terminal-blocked form thereof is obtained.

As mentioned above, the terminal-blocked form of the semicarbazide derivative of the present invention has at least one blocked terminal group derived from the terminal group $H_2NR^3N—$ in formula (1), which blocked terminal group is represented by the formula $R^9R^8C=NR^3N—$ (wherein $R^3$, $R^8$ and $R^9$ are as defined above).

In the present invention, it is necessary that when a coating composition containing a polycarbonyl compound and the semicarbazide derivative as a curing agent therefor is applied to the surface of a substrate, a cross-linking be caused to proceed between the semicarbazide group of the semicarbazide derivative and the carbonyl group of the polycarbonyl compound. Therefore, for obtaining a coating exhibiting a high cross-linking degree, the terminal blocking group ($R^9R^8C=$) of the terminal-blocked form of a semicarbazide derivative, which terminal group is derived from the monoaldehyde or monoketone used as a blocking agent, needs to be liberated in the form of the monoaldehyde or monoketone by hydrolysis of the terminal of the semicarbazide derivative.

The above-mentioned liberation of the terminal blocking group ($R^9R^8C=$) in the form of a monoaldehyde or a monoketone by hydrolysis of the terminal of the semicarbazide derivative or from a mixture of a semicarbazide derivative and a terminal-blocked form thereof can be conducted by hydrolysis and distillation before being mixed with a polycarbonyl compound. Alternatively, the liberation of the terminal blocking group in the form of a monoaldehyde or a monoketone by hydrolysis of the terminal of the semicarbazide derivative can also be conducted by a method in which the terminal-blocked form of the semicarbazide derivative or a mixture of the semicarbazide derivative and a terminal-blocked form thereof, as such, is used as a curing agent in preparing a coating composition; the coating composition thus prepared is applied to the surface of a substrate; and the terminal blocking group ($R^9R^8C=$) is allowed to be spontaneously liberated in the form of a monoaldehyde or a monoketone during the course of the curing after the application. Therefore, a monoketone having a relatively low boiling temperature, e.g., a boiling temperature of from 30 to 200° C., is preferred as a blocking agent.

The semicarbazide derivative and a terminal-blocked form thereof of the present invention is produced by reacting a polyisocyanate with hydrazine or a derivative thereof, or with a mixture of non-terminal-blocked and terminal-blocked forms of hydrazine or a derivative thereof in a molar ratio of from 1:1.5 to 1:100, preferably from 2:5 to 2:50, in terms of the molar ratio of the NCO groups (contained in the polyisocyanate) to the terminal groups represented by the following formula (11) (contained in the hydrazine or derivative thereof) or the total of non-blocked and blocked terminal groups, at 0 to 100° C., preferably 10 to 60° C. The reaction is completed in a moment when the terminal groups of hydrazine or a derivative thereof are not blocked. However, when a terminal-blocked form of hydrazine or a derivative thereof is used, the reaction is allowed to proceed for 30 minutes to 10 hours.

$$—NR^{10}NH_2 \quad (11)$$

wherein $R^{10}$ represents a hydrogen atom or a $C_1$–$C_{20}$ alkyl group.

After the reaction has been completed, the excess hydrazine or derivative thereof remaining in the obtained semicarbazide derivative or a terminal-blocked form thereof can be removed by an appropriate method, such as distillation or extraction.

The reaction for the production of the semicarbazide derivative and a terminal-blocked form thereof of the present invention can be conducted either in the presence or absence of a solvent. As a solvent, one which is inert to an NCO group or one which has a lower activity to an NCO group than the activity of the reactants can be used. Examples of solvents include ketone type solvents, such as acetone, methyl ethyl ketone, methyl isobutyl ketone and cyclohexanone; ether type solvents, such as dioxane, tetrahydrofuran and diethylene glycol dimethylether; amide type solvents, such as dimethylformamide and dimethylacetamide; lactam type solvents, such as N- methyl-2-pyrrolidone; sulfoxide type solvents, such as dimethyl sulfoxide; ester type solvents, such as ethyl acetate and cellosolve acetate; alcohols, such as t-butanol and diacetone alcohol; aromatic hydrocarbon type solvents, such as toluene and xylene; and aliphatic hydrocarbon type solvents, such as n-hexane. These solvents are used individually or in combination.

These solvents are used in an amount such that the weight ratio of the polyisocyanate to the solvent is from 0.1/99.9 to 99/1, preferably from 0.1/99.9 to 50/50.

It is preferred that the semicarbazide derivative of the present invention have a weight average molecular weight of less than 2,000, and a terminal-blocked form of the semicarbazide derivative have a weight average molecular weight of less than 3,000. When the semicarbazide derivative or a terminal-blocked form thereof has a molecular weight which is higher than the above-mentioned respective range, the cross-linking degree becomes low at the time of the formation of a coating from a coating composition containing at least one member selected from the group consisting of the semicarbazide derivative and a terminal-blocked form thereof, and a polycarbonyl compound, so that a coating having excellent toughness and water resistance cannot be obtained.

As mentioned below, a polycarbonyl compound is generally in the form of a dispersion thereof in an aqueous medium and/or a solution thereof in an aqueous medium. Therefore, from the viewpoint of preventing occurrence of coagulation at the time of the mixing of the semicarbazide derivative or terminal-blocked form thereof with the polycarbonyl compound and of improving the dispersibility of the components in the coating composition, it is preferred that the semicarbazide derivative or a terminal-blocked form thereof of the present invention be in the form of at least one member selected from the group consisting of a dispersion thereof in an aqueous medium and a solution thereof in an aqueous medium. Examples of aqueous media include water and a mixture of water and polar solvents, such as a mixture of water and acetone, a mixture of water and ether and a mixture of water, acetone and ether.

The semicarbazide derivative and/or a terminal-blocked form thereof of the present invention can be dispersed and/or dissolved in an aqueous medium by adding, while stirring, the aqueous medium to the semicarbazide derivative and/or a terminal-blocked form thereof or by adding, while stirring, the semicarbazide derivative and/or a terminal-blocked form thereof to the aqueous medium. In either case, the concentration of the semicarbazide derivative and/or a terminal-blocked form thereof in the aqueous medium may be within the range of from 0.1 to 90% by weight.

In order to improve the dispersibility and dispersion stability of or the solubility of the semicarbazide derivative represented by formula (1) or a terminal-blocked form thereof in an aqueous medium, a surfactant can be mixed with at least one member selected from the group consisting of the semicarbazide derivative and a terminal-blocked form thereof. The surfactant to be used in the present invention is, for example, at least one member selected from the group consisting of a hydrophilic group-containing compound represented by the following formula (7) and a terminal-blocked form thereof:

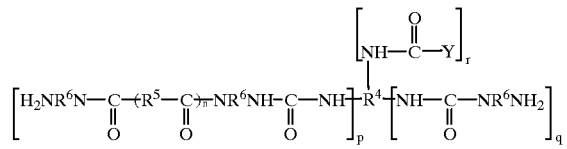

(7)

wherein $R^4$ represents a terminal isocyanate group-free polyisocyanate residue derived from a 3- to 20-mer oligomer of at least one diisocyanate selected from the group consisting of a linear or branched $C_2$–$C_{20}$ alkylene diisocyanate, a $C_5$–$C_{20}$ cycloalkylene diisocyanate which is unsubstituted or substituted with a $C_1$–$C_{18}$ alkyl group, a $C_1$–$C_8$ alkoxy group or a $C_1$–$C_6$ alkylene group, a $C_6$–$C_{20}$ arylene diisocyanate which is unsubstituted or substituted with a $C_1$–$C_{18}$ alkyl group or a $C_1$–$C_8$ alkoxy group, and a $C_8$–$C_{20}$ aralkylene diisocyanate which is unsubstituted or substituted with a $C_1$–$C_{18}$ alkyl group or a $C_1$–$C_8$ alkoxy group, or $R^4$ represents a terminal isocyanate group-free diisocyanate residue derived from said diisocyanate, or $R^4$ represents a terminal isocyanate group-free triisocyanate residue derived from a $C_2$–$C_{20}$ alkylene diisocyanate substituted with a $C_1$–$C_8$ isocyanatoalkyl group;

$R^5$ represents a linear or branched $C_2$–$C_{20}$ alkylene group, a $C_5$–$C_{20}$ cycloalkylene group, or a $C_6$–$C_{10}$ arylene group which is unsubstituted or substituted with a $C_1$–$C_{18}$ alkyl group or a $C_1$–$C_8$ alkoxy group;

each $R^6$ independently represents a hydrogen atom or a $C_1$–$C_{20}$ alkyl group;

Y represents an organic group having at least one group selected from the group consisting of a nonionic hydrophilic group, an ionic hydrophilic group and a group which is capable of converting to an ionic hydrophilic group;

n is zero or 1; and each of p and q is independently zero or a positive integer, and r is a positive integer, provided that p and q satisfy the relationship $(p+q) \geq 0$, and p, q and r satisfy the relationship $2 > (p+q+r) \leq 20$.

The terminal-blocked form of the compound represented by formula (7) has at least one blocked terminal group derived from the terminal group $H_2NR^6N-$ in formula (7), which blocked terminal group is represented by the formula $R^9R^8C=NR^6N-$, wherein each of $R^8$ and $R^9$ independently represents a hydrogen atom, a linear or branched $C_1$–$C_{20}$ alkyl group, a $C_5$–$C_{20}$ cycloalkyl group, or a $C_6$–$C_{10}$ aryl group which is unsubstituted or substituted with a $C_1$–$C_{18}$ alkyl group or a $C_1$–$C_8$ alkoxy group, with the proviso that the $R^8$ and $R^9$ together optionally form a ring structure.

That is, a semicarbazide composition comprising (α) at least one member selected from the group consisting of the semicarbazide derivative represented by formula (1) and a terminal-blocked form thereof and (β) at least one member selected from the group consisting of a hydrophilic group-containing compound represented by formula (7) and a terminal-blocked form thereof, can be advantageously used as a curing agent for a polycarbonyl compound.

With respect to this semicarbazide composition of the present invention, from the viewpoint of a good miscibility with a polycarbonyl compound, it is preferred that the semicarbazide composition be in the form of at least one member selected from the group consisting of a dispersion thereof in an aqueous medium and a solution thereof in an aqueous medium.

In the present invention, if desired, surfactants other than the hydrophilic group-containing compound represented by formula (7) or a terminal-blocked form thereof can be added to the semicarbazide derivative or a terminal-blocked form thereof. Examples of such surfactants include anionic surfactants, such as a fatty acid soap, an alkyl sulfonate, an alkyl succinate, a polyoxyethylene alkyl sulfate and a polyoxyethylene alkylaryl sulfate; nonionic surfactants, such as a polyoxyethylene alkylarylether, a sorbitan fatty acid ester of polyoxyethylene, an oxyethylene-oxypropylene block copolymer and a known reaction product obtained by reacting an ethyleneoxide with phosphoric acid; cationic surfactants containing, e.g., quaternary ammonium salt; and a high molecular weight dispersion stabilizer, such as (partially saponified)polyvinylalcohol. A mixture of these surfactants can also be used.

However, as a surfactant to be used in the present invention, the hydrophilic group-containing compound represented by formula (7) or terminal-blocked form thereof is especially preferred due to the high affinity for the semicarbazide derivative and terminal-blocked form thereof. Especially with respect to the semicarbazide composition comprising (α) at least one member selected from the group consisting of the semicarbazide derivative and a terminal-blocked form thereof, and (β) at least one member selected from the group consisting of a hydrophilic group-containing compound represented by formula (7) and a terminal-blocked form thereof, when the weight ratio of component (α) to component (β) is 10/90 to 99/1, a coating composition comprising a polycarbonyl compound and the semicarbazide composition as a curing agent therefor has especially excellent stability and curing ability.

The hydrophilic group-containing compound represented by formula (7) or a terminal-blocked form thereof of the present invention can be classified into a semicarbazide group-free, hydrophilic group-containing compound and a semicarbazide group- and hydrophilic group-containing compound.

The semicarbazide group-free, hydrophilic group-containing compound or a terminal-blocked form thereof is produced by reacting an active hydrogen-containing compound having at least one group selected from the group consisting of a nonionic hydrophilic group, an ionic hydrophilic group and a group which is capable of being converted into an ionic hydrophilic group (the at least one group being hereinafter frequently referred to simply as "hydrophilic group") with a polyisocyanate, having 3 to 20 NCO groups in a molecule thereof, which is a 3- to 20-mer oligomer of a diisocyanate, a $C_2$–$C_{20}$ alkylene diisocyanate, having 3 NCO groups in a molecule thereof, which is substituted with a $C_1$–$C_8$ isocyanatoalkyl group (triisocyanate), or the same diisocyanate per se as used for oligomarization reaction in order to obtain the above polyisocyanate. (When the above-mentioned diisocyanate is reacted with the above-mentioned active hydrogen-containing compound, $R^4$ of the obtained semicarbazide group-free hydrophilic group-containing compound is a bivalent group). In the present invention, the semicarbazide group-free, hydrophilic group-containing compound or a terminal-blocked form thereof can be used. However, from the viewpoint of obtaining a coating having a high water resistance, it is preferred to use a semicarbazide group- and hydrophilic group-containing compound, which can be obtained by reacting the above semicarbazide group-free, hydrophilic group-containing compound with hydrazine or a derivative thereof, or a mixture of non-terminal-blocked and terminal-blocked forms of hydrazine or a derivative thereof.

The diisocyanate can be the same as used for producing the semicarbazide derivative represented by formula (1) or a terminal-blocked form thereof. That is, the diisocyanate can be at least one diisocyanate selected from the group consisting of a linear or branched $C_2$–$C_{20}$ alkylene diisocyanate, a $C_5$–$C_{20}$ cycloalkylene diisocyanate which is unsubstituted or substituted with a $C_1$–$C_{18}$ alkyl group, a $C_1$–$C_8$ alkoxy group or a $C_1$–$C_6$ alkylene group, a $C_6$–$C_{20}$ arylene diisocyanate which is unsubstituted or substituted with a $C_1$–$C_{18}$ alkyl group or a $C_1$–$C_8$ alkoxy group, and a $C_8$–$C_{20}$ aralkylene diisocyanate which is unsubstituted or substituted with a $C_1$–$C_{18}$ alkyl group or a $C_1$–$C_8$ alkoxy group.

Illustrative examples of methods for producing a semicarbazide composition comprising (α) at least one member selected from the group consisting of the semi-carbazide derivative represented by formula (1) and a terminal-blocked form thereof and (β) at least one member selected from the group consisting of a hydrophilic group-containing compound represented by formula (7) and a terminal-blocked form thereof, include the two methods described below, which can be employed alone or in combination. However, the production methods are not limited to these two methods.

Method [I]: a method in which a mixture of component (α) and component (β) is obtained in a single reaction system.

Method [II]: a method in which component (β) is first produced, and the obtained component (β) is then mixed with component (α) which has been separately produced.

First, method [I] is illustrated below.

In method [I], the above-mentioned polyisocyanate or a diisocyanate substituted with an isocyanatoalkyl group (triisocyanate) is reacted with the above-mentioned active hydrogen-containing compound having a hydrophilic group in a molar ratio of NCO groups to hydrophilic groups in the range of from 1.1/1 to 500/1, preferably from 2/1 to 100/1, under substantially water-free conditions at a temperature in the range of from about 0° C. to about 130° C., preferably from about 20° C. to about 100° C. for about 30 minutes to about 10 hours (Reaction 1). Subsequently, the resultant reaction product is reacted with hydrazine or a derivative thereof, or a mixture of non-terminal-blocked and terminal-blocked forms of hydrazine or a derivative thereof under substantially the same reaction conditions as in the reaction of a polyisocyanate with hydrazine or a derivative thereof for the production of the semicarbazide derivative represented by formula (1) (Reaction 2). As a result, a semicarbazide composition comprising compound (α) and compound (β) can be obtained in a single reaction system.

The above-mentioned reactions can be conducted either in the presence or absence of a solvent.

As a solvent, those which are inert to an NCO group or those which have a lower activity to an NCO group than the activity of the reactants can be used. Examples of solvents include ketone type solvents, such as acetone, methyl ethyl ketone, methyl isobutyl ketone and cyclohexanone; ether type solvents, such as dioxane, tetrahydrofuran and diethylene glycol dimethylether; amide type solvents, such as dimethylformamide and dimethylacetamide; lactam type solvents, such as N-methyl-2-pyrrolidone; sulfoxide type solvents, such as dimethyl sulfoxide; ester type solvents, such as ethyl acetate and cellosolve acetate; alcohols, such as t-butanol and diacetone alcohol; aromatic hydrocarbon type solvents, such as toluene and xylene; and aliphatic hydrocarbon type solvents, such as n-hexane. These solvents are used individually or in combination.

These solvents can be used in an amount such that each of the weight ratio of the polyisocyanate or triisocyanate to the solvent (in Reaction 1) and the weight ratio of the reaction product of the polyisocyanate or triisocyanate with an active hydrogen-containing compound to the solvent (in Reaction 2) is from 0.1/99.9 to 99/1, preferably from 0.1/99.9 to 50/50.

If desired, the above-mentioned reactions may be conducted by an appropriate method in which a catalyst is used. Examples of catalysts include metal salts of organic or inorganic acid, such as dibutyl tin laurate, tin primary octylate and lead octylate; organic metal derivatives; organic tertiary amines, such as triethylamine and triethylene diamine; and diazabicycloundecenoic catalysts.

With respect to the active hydrogen-containing compound having a hydrophilic group, that is, at least one group selected from the group consisting of a nonionic hydrophilic group, an ionic hydrophilic group and a group which is capable of being converted into an ionic hydrophilic group, examples thereof are mentioned below.

Examples of those having a nonionic hydrophilic group include a polyethylene glycol monoalkyl ether represented by formula (12):

(12)

wherein $R^{11}$ represents a $C_1$–$C_{25}$ alkyl group;
and n is an integer of from 5 to 80, polyether polyols, such as polyethylene glycol, polyoxyethylene-oxypropylene (random and/or block) glycol and polyoxyethylene-oxytetramethylene (random and/or block) glycol. Of these, the polyethylene glycol monoalkyl ether is preferred since the polyether polyols have a tendency to undergo a chain extension reaction with a polyisocyanate, causing an increase in the molecular weight.

Preferable examples of active hydrogen-containing compounds having an ionic hydrophilic group include carboxylic acids or sulfonic acids, which are active hydrogen-containing compounds having an anionic group, and amine salts or alkali metal salts thereof; and onium salts, which are active hydrogen-containing compounds having a cationic group.

As an active hydrogen-containing compound having an anionic group, for example, an active hydrogen-containing compound having an acid group which is capable of being converted into an anionic group may also be used. In this case, the acid group of the active hydrogen-containing compound can be converted into an anionic group by neutralizing the acid group with a base at the time of the production of the above-mentioned semicarbazide composition or at the time of dispersing and/or dissolving the above-mentioned semicarbazide composition into an aqueous medium. It is preferred that the neutralization be conducted at the time of dispersing and/or dissolving the semicarbazide composition in an aqueous medium.

Examples of active hydrogen-containing compounds having an acid group which is capable of being converted into an anionic group include monohydroxycarboxylic acids, such as lactic acid, glycol acid, 4-hydroxybutyric acid and p-phenolcarboxylic acid; amino acids, such as glycine, alanine, aspartic acid and β-alanine; monohydroxysulfonic acids, such as p-phenolsulfonic acid; and aminosulfonic acids, such as taurine; and α,α-dimethylol alkanoic acids, such as α,α'-dimethylol propionic acid and α,α'-dimethylol acetic acid. They are used individually or in combination.

Of these, the monohydroxycarboxylic acids, amino acids, monohydroxysulfonic acids and aminosulfonic acids are preferred since the α,α'-dimethylol alkanoic acids have a tendency to undergo a chain extension reaction with a polyisocyanate, causing an increase in the molecular weight, so that the obtained semicarbazide composition disadvantageously has a high viscosity which is not suitable for a curing agent.

Examples of bases which can be used for the neutralization of the above-mentioned acid group which is capable of being converted into an anionic group include amine compounds, such as triethylamine, ammonia, diethanolamine, dimethylaminoethanol, methyldiethanolamine and dibutylamine; and hydroxides of alkali metals, such as KOH, NaOH and LiOH. These bases are used individually or in combination.

As an active hydrogen-containing compound having a cationic group, for example, an active hydrogen-containing compound having a base which is capable of being converted into a cationic group may also be used. In this case, the base of the active hydrogen-containing compound can be converted into a cationic group by neutralizing the base with an acid group at the time of the production of the above-mentioned semicarbazide composition or at the time of dispersing and/or dissolving the above-mentioned semicarbazide composition into an aqueous medium. In the case of an active hydrogen-containing compound which has a tertiary amino group, the tertiary amino group can be converted into a quaternary amino group (which is a cationic group) by using an alkylating agent at the time of the production of the above-mentioned semicarbazide composition or at the time of dispersing and/or dissolving the above-mentioned semicarbazide composition into an aqueous medium. It is preferred that the neutralization be conducted at the time of dispersing and/or dissolving the semicarbazide composition in an aqueous medium.

Examples of active hydrogen-containing compounds having a base which is capable of being converted into a cationic group include N-alkyldialkanolamines, such as N-methyldiethanolamine, N-butyldiethanolamine and addition products thereof with a $C_2$–$C_4$ alkyleneoxide (e.g. ethylene oxide and propylene oxide) ; and N,N-dialkylmonoalkanolamines, such as N,N-dimethylethanolamine and N,N-diethylethanolamine. These active hydrogen-containing compounds are used individually or in combination. Of these, N,N-dialkylmonoalkanolamines, such as N,N-dimethylethanolamine and N,N-diethylethanolamine are especially preferred.

Examples of acids which can be used for the neutralization of the bases of these active hydrogen-containing compounds include acetic acid, lactic acid, hydrochloric acid, phosphoric acid and sulfuric acid. These acids are used individually or in combination. Examples of alkylating agents include dimethylsulfuric acid, diethylsulfuric acid, methyl chloride, methyl iodide and benzyl chloride.

Next, method [II] is illustrated below.

As mentioned above, in method [II], component (β), i.e., at least one member selected from the group consisting of a hydrophilic group-containing compound represented by formula (7) and a terminal-blocked form thereof is first produced, and the obtained component (β) is then mixed with a separately prepared component (α), i.e., at least one member selected from the group consisting of the semicarbazide derivative represented by formula (1) and a terminal-blocked form thereof.

As illustrative examples of methods for obtaining component (β), there can be mentioned:
  a method in which a diisocyanate having 2 NCO groups in a molecule thereof is reacted with an active hydrogen-containing compound having at least one group (hydrophilic group) selected from the group consisting of a nonionic hydrophilic group, an ionic hydrophilic group and a group which is capable of being converted into an ionic hydrophilic group, in a molar ratio of NCO groups to hydrophilic groups of from 1/1 to 10/1 and then, the resultant reaction product is reacted with hydrazine or a derivative thereof; and
  a method in which a polyisocyanate having from 3 to 20 NCO groups in a molecule thereof or a triisocyanate having 3 NCO groups in a molecule thereof is reacted with an active hydrogen-containing compound having at least one group (hydrophilic group) selected from the group consisting of a nonionic hydrophilic group, an ionic hydrophilic group and a group which is capable of being converted into an ionic hydrophilic group, in a molar ratio of NCO groups to hydrophilic groups of from 0.1/1 to 1.1/1 and then, the resultant reaction product is reacted with hydrazine or a derivative thereof.

In method [II], as the polyisocyanate having from 3 to 20 NCO groups in a molecule thereof and the triisocyanate having 3 NCO groups in a molecule thereof, the same polyisocyanate and triisocyanate as used for producing the semicarbazide derivative represented by formula (1) and a terminal-blocked form thereof, can be used. Also, in method [II], as the diisocyanate having 2 NCO groups in a molecule thereof, the same diisocyanate as used for producing the polyisocyanate can be used.

Two different types of component ($\beta$) are obtained by the above-mentioned two types of methods. The obtained two types of component ($\beta$) can be individually mixed with component ($\alpha$), or a mixture of them can be mixed with component (a).

In method [II], as the active hydrogen-containing compound having at least one group (hydrophilic group) selected from the group consisting of a nonionic hydrophilic group, an ionic hydrophilic group and a group which is capable of being converted into an ionic hydrophilic group, the same active hydrogen-containing compound, as used in method [I], can be used.

In method [II], first, a diisocyanate having 2 NCO groups in a molecule thereof, a polyisocyanate having from 3 to 20 NCO groups in a molecule thereof or a triisocyanate having 3 NCO groups in a molecule thereof is reacted with an active hydrogen-containing compound having at least one group (hydrophilic group) selected from the group consisting of a nonionic hydrophilic group, an ionic hydrophilic group and a group which is capable of being converted into an ionic hydrophilic group, under substantially the same reaction conditions as in method [I], to thereby obtain a reaction product.

The above-mentioned reaction can be carried out in the absence or presence of a solvent, using a catalyst, if desired. As the solvents and the catalysts, the same as used in method [I] can be used.

Next, the obtained reaction product is reacted with hydrazine or a derivative thereof, or a mixture of terminal-blocked and non-terminal-blocked forms of hydrazine or a derivative thereof, in a molar ratio of from 1:1.5 to 1:100, preferably from 2:5 to 2:50 in terms of the NCO groups in the reaction product to the terminal groups of the hydrazine or derivative thereof and the blocked terminal groups derived therefrom, under substantially the same conditions as used for the reaction of a polyisocyanate with hydrazine or a derivative thereof, or with a mixture of terminal-blocked and non-terminal-blocked forms of hydrazine or a derivative thereof in the production of a semicarbazide derivative represented by formula (1) or a terminal-blocked form thereof. As a result, component ($\beta$) is obtained.

The thus obtained component ($\beta$) is mixed with component ($\alpha$) which has been separately prepared, in a weight ratio of from 10/90 to 99/1, to thereby obtain a semicarbazide composition of the present invention.

The semicarbazide composition obtained according to method [I] or [II] above can be dispersed and/or dissolved in an aqueous medium by adding, while stirring, the aqueous medium to the semicarbazide composition or by adding, while stirring, the semicarbazide composition to the aqueous medium. In either case, the concentration of the semicarbazide composition in the aqueous medium can be within the range of from 0.1 to 90% by weight. Also, if desired, the aforementioned surfactants can be added in order to improve the dispersibility and dispersion stability of the semicarbazide composition.

Since each of ($\alpha$) at least one member selected from the group consisting of a semicarbazide derivative and terminal-blocked form thereof according to the present invention and ($\delta$) the semicarbazide composition of the present invention has excellent compatibility with a polycarbonyl compound ($\gamma$), a coating composition comprising ($\gamma$) a polycarbonyl compound and, as a curing agent therefor, ($\alpha$) at least one member selected from the group consisting of the semicarbazide derivative and terminal-blocked form thereof, or the above-mentioned ($\delta$) semicarbazide composition, has not only excellent cold-curing ability and storage stability, but is also capable of forming a coating having various excellent properties including excellent hardness, water resistance and stain resistance, which have conventionally been unable to be achieved.

According to the present invention, by mixing the above-mentioned ($\alpha$) at least one member selected from the group consisting of the semicarbazide derivative and terminal-blocked form thereof or the above-mentioned ($\delta$) semicarbazide composition, with ($\gamma$) a polycarbonyl compound comprising at least one member selected from the group consisting of a carbonyl group-containing polyurethane, an acetoacetylated polyvinyl alcohol, an acetoacetylated hydroxyalkyl cellulose and a carbonyl group-containing copolymer of 0.1 to 30% by weight of (a) a carbonyl group-containing ethylenically unsaturated monomer with 70 to 99.9% by weight of (b) an ethylenically unsaturated monomer copolymerizable with the monomer (a), a coating composition which has not only excellent cold-curing ability and storage stability, but is also capable of forming a coating having various excellent properties including excellent hardness, water resistance and stain resistance, can be obtained.

In the coating composition of the present invention, the weight ratio of component ($\alpha$) or component ($\delta$) to component ($\gamma$) is preferably in the range of from 0.1/99.9 to 90/10, more preferably in the range of from 0.5/99.5 to 30/70.

With respect to polycarbonyl compound ($\gamma$) for example, a carbonyl group-containing polyurethane can be used, which can be produced from a carbonyl group-containing monoalcohol and/or polyalcohol, such as a hydroxyacetone disclosed in Unexamined Japanese Patent Application Laid-Open Specification No. 2-238015.

In the coating composition of the present invention, it is preferred that component ($\gamma$) be a carbonyl group-containing copolymer of 0.1 to 30% by weight of (a) the carbonyl group-containing ethylenically unsaturated monomer with 70 to 99.9% by weight of (b) the ethylenically unsaturated monomer copolymerizable with the monomer (a).

Examples of carbonyl group-containing ethylenically unsaturated monomers (a) include diacetone acrylamide, diacetone methacrylamide, acrolein, vinyl methyl ketone, acetoacetoxy ethyl methacrylate, acetoacetoxy ethyl acrylate and formylstyrol. These carbonyl group-containing ethylenically unsaturated monomers are used individually or in combination.

In the present invention, examples of ethylenically unsaturated monomers (b) copolymerizable with carbonyl group-containing ethylenically unsaturated monomers (a) include acrylic acid ester, methacrylic acid ester, carboxyl group-containing ethylenically unsaturated monomers, acrylamide monomers, methacrylamide monomers and vinyl cyanides.

Examples of the above-mentioned (meth)acrylic acid esters which can be used in the present invention include a $C_1$–$C_{18}$ alkyl ester of (meth)acrylic acid, a $C_1$–$C_{18}$ hydroxyalkyl ester of (meth)acrylic acid, a (poly)oxyethylene mono (meth)acrylate having 1 to 100 ethylene oxide groups, a (poly)oxypropylene mono(meth)acrylate having 1 to 100 propylene oxide groups and a (poly)oxyethylene di(meth) acrylate having 1 to 100 ethylene oxide groups.

Specific examples of $C_1$–$C_{18}$ alkyl esters of (meth)acrylic acid include methyl (meth)acrylate, ethyl (meth)acrylate, n-butyl (meth)acrylate, 2-ethylhexyl (meth)acrylate, methylcyclohexyl (meth)acrylate and dodecyl (meth)acrylate.

Specific examples of $C_1$–$C_{18}$ hydroxyalkyl esters of (meth)acrylic acid include 2-hydroxyethyl (meth)acrylate, 2-hydroxypropyl (meth)acrylate, 2-hydroxycyclohexyl (meth)acrylate and hydroxydodecyl (meth)acrylate.

Specific examples of (poly)oxyethylene mono(meth) acrylates include ethylene glycol (meth)acrylate, ethylene glycol methoxy(meth)acrylate, diethylene glycol (meth) acrylate, diethylene glycol methoxy(meth)acrylate, tetraethylene glycol (meth)acrylate and tetraethylene glycol methoxy(meth)acrylate.

Specific examples of (poly)oxypropylene mono(meth) acrylates include propylene glycol (meth)acrylate, propylene glycol methoxy(meth)acrylate, dipropylene glycol (meth)acrylate, dipropylene glycol methoxy(meth)acrylate, tetrapropylene glycol (meth)acrylate and tetrapropylene glycol methoxy(meth)acrylate.

Specific examples of (poly)oxyethylene di(meth)acrylates include ethylene glycol di(meth)acrylate, diethylene glycol di(meth)acrylate, diethylene glycol methoxy(meth)acrylate and tetraethylene glycol di(meth)acrylate.

Specific examples of carboxyl group-containing ethylenically unsaturated monomers include acrylic acid, methacrylic acid, itaconic acid, fumaric acid, maleic acid and a half ester thereof and crotonic acid. Specific examples of (meth)acrylamide monomers include (meth)acrylamide, N-methylol (meth)acrylamide, N-butoxymethyl (meth) acrylamide. Specific examples of vinyl cyanides include (meth)acrylonitrile.

Other specific examples of ethylenically unsaturated monomers (b) copolymerizable with carbonyl group-containing ethylenically unsaturated monomers (a) include olefins, such as ethylene, propylene and isobutylene; dienes, such as butadiene; haloolefins, such as vinyl chloride and vinylidene chloride; vinyl esters of carboxylic acid, such as vinyl acetate, vinyl propionate, n-vinyl butyrate, vinyl benzoate, p-t-butyl vinyl benzoate, vinyl pivalate acid vinyl, 2-vinyl ethyl hexanoate, vinyl ester versatic acid and lauric acid vinyl; isopropenyl esters of carboxylic acid, such as isopropenyl acetate and isopropenyl propionate; vinyl ethers, such as ethyl vinyl ether, isobutyl vinyl ether and cyclohexyl vinyl ether; aromatic vinyl compounds, such as stylene and vinyltoluene; allyl esters, such as allyl acetate and allyl benzoate; allyl ethers, such as allyl ethyl ether, allyl glycidyl ether and allyl phenyl ether; and (meth) acryloxypropyltrimethoxysilane; 4-(meth)acryloyloxy-2,2, 6,6,-tetramethylpiperidine; 4-(meth)acryloyloxy-1,2,2,6,6,-pentamethylpiperidine; perfluoromethyl (meth)acrylate; perfluoropropyl (meth)acrylate; perfluoropropyl methyl (meth)acrylate; vinyl pyrrolidone; trimethylol propane tri (meth)acrylate; glycidyl(meth)acrylate; 2,3-cyclohexeneoxide (meth)acrylate; and allyl(meth)acrylate. These ethylenically unsaturated monomers (b) copolymerizable with carbonyl group-containing ethylenically unsaturated monomers (a) are used individually or in combination.

The coating composition of the present invention is preferably in the form of at least one member selected from the group consisting of a dispersion thereof in an aqueous medium and a solution thereof in an aqueous medium.

When the coating composition of the present invention is provided in the form of at least one member selected from the group consisting of a dispersion of components (α) and (1) in an aqueous medium and a solution of components (α) and (γ) in an aqueous medium, it is preferred that the coating composition be one obtained by mixing component (α) and component (γ), wherein each of component (α) and component (γ) is in the form of at least one member selected from the group consisting of a dispersion thereof in an aqueous medium and a solution thereof in an aqueous medium, and that the total weight of components (α) and (γ) be within the range of from 0.1 to 70% by weight, based on the weight of the dispersion and/or the solution of the coating composition. With respect to the dispersion and/or solution of component (α) to be mixed, it is preferred that the amount of component (α) be within the range of from 0.1 to 90% by weight, based on the weight of the dispersion and/or solution thereof. With respect to the dispersion and/or solution of component (γ) to be mixed, it is preferred that the amount of component (γ) be within the range of from 0.1 to 70% by weight, based on the weight of the dispersion and/or solution thereof.

Likewise, when the coating composition of the present invention is provided in the form of at least one member selected from the group consisting of a dispersion of components (δ) and (γ) in an aqueous medium and a solution of components (δ) and (γ) in an aqueous medium, it is preferred that the coating composition be one obtained by mixing component (δ) and component (γ), wherein each of component (δ) and component (γ) is in the form of at least one member selected from the group consisting of a dispersion thereof in an aqueous medium and a solution thereof in an aqueous medium, and that the total weight of components (δ) and (γ) be within the range of from 0.1 to 70% by weight, based on the weight of the dispersion and/or the solution of the coating composition. With respect to the dispersion and/or solution of component (δ) to be mixed, it is preferred that component (δ) be within the range of from 0.1 to 90% by weight, based on the weight of the dispersion and/or solution thereof. With respect to the dispersion and/or solution of component (γ) to be mixed, it is preferred that component (γ) be within the range of from 0.1 to 70% by weight, based on the weight of the dispersion and/or solution thereof.

With respect to the above-mentioned coating composition in the form of a dispersion of components (α) and (γ) and/or a solution of components (α) and (γ), and to the above-mentioned coating composition in the form of a dispersion of components (δ) and (γ) and/or a solution of components (δ) and (γ), it is preferred that component (γ) be a carbonyl group-containing copolymer of 0.1 to 30% by weight of (a) the carbonyl group-containing ethylenically unsaturated monomer with 70 to 99.9% by weight of (b) the ethylenically unsaturated monomer copolymerizable with monomer (a).

In the present invention, it is preferred that the carbonyl group-containing copolymer as component (γ) in the above-mentioned dispersion and/or solution be one which is obtained by at least one method selected from the group consisting of suspension polymerization, emulsion polymerization and solution polymerization of (a) the carbonyl group-containing ethylenically unsaturated monomer and (b) the ethylenically unsaturated monomer copolymerizable with monomer (a). It is especially preferred that the carbonyl group-containing copolymer as component (γ) be in the form of a latex which is obtained by an emulsion polymerization of (a) the carbonyl group-containing ethylenically unsaturated monomer and (b) the ethylenically unsaturated monomer copolymerizable with the monomer (a).

In the present invention, with respect to the copolymerization of (α) the carbonyl group-containing ethylenically unsaturated monomer with (b) the ethylenically unsaturated monomer copolymerizable with monomer (a), it is especially preferred that the copolymerization be conducted in the presence of (c) an emulsifier comprising at least one member selected from the group consisting of a sulfonic acid group-containing ethylenically unsaturated monomer and a sulfonate group-containing ethylenically unsaturated monomer.

In the present invention, it is preferred that the emulsifier (c) comprising at least one member selected from the group consisting of a sulfonic acid group-containing ethylenically unsaturated monomer and a sulfonate group-containing ethylenically unsaturated monomer be selected from radically polymerizable double bond-containing compounds having a sulfonic acid group, or an ammonium or an alkali metal salt thereof (i.e., ammonium sulfonate group or alkali metal sulfonate group).

Among these compounds, more preferred are radically polymerizable double bond-containing compounds having a substituent selected from the group consisting of a $C_1$–$C_{20}$ alkyl group, a $C_2$–$C_4$ alkyl ether group, a poly-$C_2$–$C_4$ alkyl ether group, a $C_6$ or $C_{10}$ aryl group, and a succinic acid group, each of which is substituted with a sulfonic acid group which is in the form of an ammonium, a sodium or a potassium salt thereof, or vinyl sulfonate compounds having a vinyl group bonded to a sulfonic acid group which is in the form of an ammonium, a sodium or a potassium salt thereof.

Specific examples of compounds having a succinic acid group which is substituted with a sulfonic acid group which is in the form of an ammonium, a sodium or a potassium salt thereof include allylsulfosuccinates which, for example, can be represented by a formula selected from the following formulae (16), (17), (18) and (19):

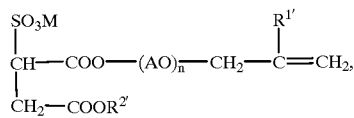
(16)

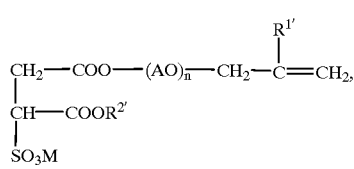
(17)

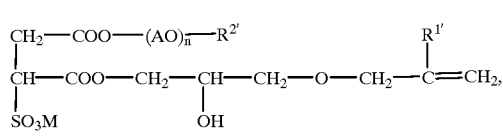
(18)

and

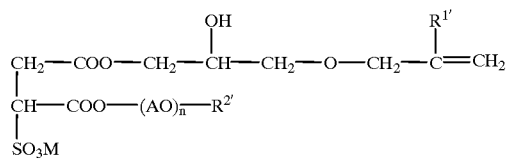
(19)

wherein $R^1$ represents a hydrogen atom or a methyl group; $R^2$ represents a hydrocarbon group, such as a $C_1$–$C_{20}$ alkyl group, a $C_1$–$C_{20}$ alkenyl group, a $C_5$–$C_{12}$ cycloalkyl group, a $C_5$–$C_{10}$ aryl group or a $C_6$–$C_{19}$ aralkyl group, each of which is unsubstituted or partially substituted with a hydroxyl group, a carboxyl group or the like, or an organic group containing an alkylene oxide, such as a polyoxyalkylene alkyl ether group (in which the alkylene moiety has 2 to 4 carbon atoms and the alkyl moiety has 0 to 20 carbon atoms) or a polyoxyalkylene alkylphenyl ether group (in which the alkylene moiety has 2 to 4 carbon atoms and the alkyl moiety has 0 to 20 carbon atoms); A represents an unsubstituted or substituted $C_2$–$C_4$ alkylene group; n represents an integer of from 0 to 200; and M represents an ammonium group, a sodium atom or a potassium atom.

Specific examples of commercially available products which comprise compounds represented by formulae (16) and (17) above include Eleminol® JS-2 (manufactured and sold by SANYO CHEMICAL INDUSTRIES, LTD., Japan). Specific examples of commercially available products which comprise compounds represented by formulae (18) and (19) above include Latemul® S-120, S-180A and S-180 (manufactured and sold by Kao Corp., Japan).

Specific examples of compounds having a $C_2$–$C_4$ alkyl ether group or a poly-$C_2$–$C_4$ alkyl ether group, each of which is substituted with a sulfonic acid group which is in the form of an ammonium, a sodium or a potassium salt thereof, include compounds represented by a formula selected from the following formulae (20) and (21):

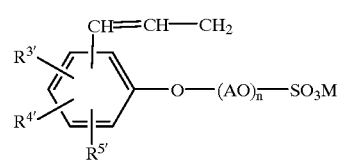
(20)

wherein $R^3$ represents a $C_6$–$C_{18}$ alkyl, alkenyl or aralkyl group; $R^4$ represents a $C_6$–$C_{18}$ alkyl, alkenyl or aralkyl group; $R^5$ represents a hydrogen atom or a propenyl group; A represents a $C_2$–$C_4$ alkylene group; n represents an integer of from 1 to 200; and M represents an ammonium group, a sodium atom or a potassium atom, and

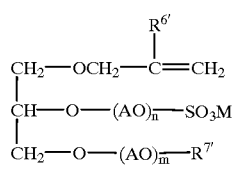
(21)

wherein $R^6$ represents a hydrogen atom or a methyl group; $R^7$ represents a $C_8$–$C_{24}$ alkyl or acyl group; A represents a $C_2$–$C_4$ alkylene group; n represents an integer of from 0 to 20; m represents an integer of from 0 to 50; and M represents an ammonium group, a sodium atom or a potassium atom.

Specific examples of alkylphenol ether compounds represented by formula (20) above include Aquaron® HS-10 (manufactured and sold by Dai-ichi Kogyo Seiyaku Co., Ltd., Japan). Specific examples of compounds represented by formula (21) above include Adeka Rea soap® SE-1025N (manufactured and sold by ASAHI DENKA KOGYO K.K., Japan).

Specific examples of compounds having a $C_6$ or $C_{10}$ aryl group which is substituted with a sulfonate group include a p-styrenesulfonic acid which is in the form of an ammonium, a sodium or a potassium salt thereof. Specific examples of compounds having a $C_1$–$C_{20}$ alkyl group which is substituted with a sulfonate group include methylpropanesulfon(meth)acrylamide which is in the form of an ammonium, a sodium or a potassium salt thereof. Specific examples of sulfonate group-containing compounds other than mentioned above include a vinyl sulfonate compound having a vinyl group bonded to a sulfonic acid group which is in the form of an ammonium, a sodium or a potassium salt thereof.

The ethylenically unsaturated monomer as emulsifier (c) can be present in the emulsion in any of the following states:
(i) the ethylenically unsaturated monomer is present in the form of a copolymerized product thereof with the emulsified particles of the emulsion containing a copolymer of monomer (a) with monomer (b), which copolymerized product is formed by radical polymerization;
(ii) the ethylenically unsaturated monomer is adsorbed on the emulsified particles of the emulsion or present in the aqueous phase of the emulsion, in the form of an unreacted monomer; and
(iii) the ethylenically unsaturated monomer is adsorbed on the emulsified particles of the emulsion or present in the aqueous phase of the emulsion, in the form of a copolymer thereof with a water-soluble monomer or a hydrophilic monomer which is a by-product in the emulsion, or in the form of a polymer of the ethylenically unsaturated monomers. In this connection, it is noted that the higher the ratio of the ethylenically unsaturated monomers which are present in state (i) above, the higher the water resistance of the coating formed from a coating composition prepared using the emulsion containing a copolymer of monomer (a) and monomer (b).

The ethylenically unsaturated monomer as emulsifier (c) can be identified by subjecting a coating obtained from the emulsion to a pyrolysis gas chromatography/mass spectrometry (Py-GC-MS) or a pyrolysis mass spectrometry (Py-MS). Alternatively, the ethylenically unsaturated monomers can be identified by a method in which the aqueous phase is separated from the emulsion and the residue is subjected to fast atom bombardment mass spectrometry (FAB mass spectrometry).

In the present invention, in addition to the above-mentioned emulsifier (c) which is selected from the group consisting of a sulfonic acid group- or sulfonate group-containing ethylenically unsaturated monomer and a mixture thereof, a conventional surfactant can be used in combination with emulsifier (c). Examples of conventional surfactants which can be used in combination with emulsifier (c) include anionic surfactants, such as a fatty acid soap, an alkyl sulfonate, an alkyl sulfosuccinate, a polyoxyethylene alkyl sulfate, a polyoxyethylene alkylaryl sulfate; non-reactive nonionic surfactants, such as a polyoxyethylene alkylaryl ether, a sorbitan fatty acid ester of polyoxyethylene and an oxyethylene-oxypropylene block copolymer; and reactive nonionic surfactants, such as α-{1-[(allyloxy)methyl]-2-(nonylphenoxy)ethyl}-ω-hydroxypolyoxyethylene [e.g., Adeka Rea soap NE-20, NE-30 and NE-40 (manufactured and sold by ASAHI DENKA KOGYO K.K., Japan)], a polyoxyethylene alkylpropenylphenylether [e.g., Aquaron RN-10, RN-20, RN-30 and RN-50 (manufactured and sold by Dai-ichi Kogyo Seiyaku Co., Ltd., Japan)].

With respect to the amount of such a conventional surfactant, if any, in terms of % by weight, based on the weight of the emulsion containing a copolymer of monomer (a) and monomer (b): an anionic surfactant can be used in an amount of 0.5% by weight or less, preferably 0.25% by weight or less, more preferably 0.1% by weight or less; and a non-reactive nonionic surfactant or a reactive nonionic surfactant can be used in an amount of 2.0% by weight or less, preferably 1.0% by weight or less, more preferably 0.5% by weight or less. When the conventional surfactants are used in amounts which exceed the above ranges, a coating obtained from the emulsion has disadvantageously low water resistance.

In the coating composition of the present invention comprising component (α) or (δ) and component (γ), the total weight of a surfactant inclusive of emulsifier (c) is preferably 0.1 to 20% by weight.

In the production of polycarbonyl compound (γ), a compound which is decomposable by heat or by a reducing agent to generate radicals and thereby initiate an addition polymerization reaction of the ethylenically unsaturated monomers (a) and (b), can be advantageously employed as a radical polymerization catalyst. Examples of such compounds include a water-soluble or oil-soluble persulfates, peroxides, and azobis compounds. Specific examples of such compounds include potassium persulfate, sodium persulfate, ammonium persulfate, hydrogen peroxide, t-butyl hydroperoxide, t-butyl peroxybenzoate, 2,2-azobisisobutyronitrile, 2,2-azobis(2-diaminopropane) hydrochloride and 2,2-azobis(2,4-dimethylvaleronitrile). The radical polymerization catalyst is generally used in an amount of from 0.1 to 1% by weight, based on the total weight of the ethylenically unsaturated monomers (a) and (b).

Generally, it is preferred that polymerization be conducted at a temperature of from 65 to 90° C. under atmospheric pressure. However, the polymerization can be conducted under high pressure in a closed system, so as to, for example, prevent the monomers from being vaporized at the polymerization temperature. The polymerization time comprises an introduction time and a maturation (cooking) time. With respect to the introduction time, when each of the materials is introduced to a reaction system at a time, the introduction time is generally several minutes. When the raw materials are stepwise introduced to a reaction system, the introduction of the raw materials is conducted in a manner such that the heat generated by the polymerization reaction can be removed. Therefore, in this case, the introduction time may vary, depending on the desired content of the polymer in a final emulsion. However, the introduction time is generally 10 minutes or more. With respect to the maturation (cooking) time, it is preferred that the maturation time be 10 minutes or more. When the polymerization time is shorter than the period of time as mentioned above, there is a danger that the raw materials remain unreacted. When it is desired to increase the rate of polymerization or when it is desired to perform a polymerization reaction at a temperature as low as 70° C. or less, it is advantageous to use a reducing agent, such as sodium bisulfite, ferrous chloride, ascorbate and Rongalit, in combination with a radical polymerization catalyst. Further, if desired, in order to control the molecular weight of the polymer, a chain transfer agent, such as dodecylmercaptan, can be used.

In the present invention, from the viewpoint of maintaining the stability of the polycarbonyl compound ($\gamma$) in a coating composition for a prolonged period of time, it is preferred that the pH value of the coating composition be adjusted to 4 to 10, using ammonia, sodium hydroxide, potassium hydroxide, amines, such as dimethylaminoethanol, and acids, such as hydrochloric acid, sulfuric acid, acetic acid and lactic acid.

Also, in the coating composition of the present invention, if desired, not more than 90% by weight of the polycarbonyl compound can be substituted with a polyepoxy compound. By incorporating a polyepoxy compound, the water resistance of the coating obtained will be further improved.

As the polyepoxy compound, there can be mentioned, for example, an epoxy group-containing copolymer obtained by copolymerizing an epoxy group-containing ethylenically unsaturated monomer, such as glycidyl (meth)acrylate, with another unsaturated monomer, using a bulk polymerization method, a suspension polymerization method, an emulsion polymerization method, a solution polymerization method and the like; bisphenol A type epoxy resin; bisphenol F type epoxy resin; a cycloaliphatic epoxy resin; a glycidyl ester epoxy resin; a glycidyl amine epoxy resin; a hydantoin type epoxy resin; an aqueous dispersion of triglycidylisocyanurate; and mixtures thereof.

The coating composition of the present invention, if desired, can contain additives, which are customarily added to aqueous coating materials, such as pigments, filling agents, dispersants, light stabilizers, wetting agents, viscosity bodying agents, Theological property controlling agents, antifoamers, plasticizers, film forming aids, rust preventive agents, dyes, antiseptics, and the like. The additives may be used individually or in combination, according to the use of the coating composition, in amounts which are customarily employed.

As mentioned above, since the coating composition of the present invention has not only excellent cold-curing ability and storage stability, but is also capable of forming a coating having various excellent properties including excellent hardness, toughness, water resistance, stain resistance and the like, the coating composition can advantageously be used as a paint, an undercoating or a finish coating material for building materials, an adhesive, a pressure-sensitive adhesive, a processing agent for papers, or a finish coating material for textile fabrics.

BEST MODE FOR CARRYING OUT THE INVENTION

Hereinbelow, the present invention will be described in more detail with reference to the following Referential Examples, Examples and Comparative Examples, but they should not be construed as limiting the scope of the present invention.

In the Referential Examples, Examples and Comparative Examples, the "part(s)" are given by weight.

Further, in the Examples and Comparative Examples, measurement and evaluation of various properties were made in accordance with the following methods.

1. Molecular Weight Distribution:

Molecular weight distribution was measured by gel permeation chromatography, using a calibration curve of standard polystyrene samples.

(Equipments used)

Apparatus: HLC-8020 LC-3A (manufactured and sold by Tosoh Corp., Japan)

Column: TSKgel G-5000 HXL
TSKgel G-4000 HXL
TSKgel G-2000 HXL
(manufactured and sold by Tosoh Corp., Japan) Data processor: SC 8010 (manufactured and sold by Tosoh Corp., Japan) Carrier: Tetrahydrofuran 2. Infrared Ray Absorption Spectra were Measured by FT/IR-5300 (manufactured and sold by Japan Spectroscopic Co. Ltd., Japan).

3. Curing Ability of Coating Composition

In Examples 9 to 11 and Comparative Examples 1 to 4, the appearance of the coating formed on a glass plate was evaluated in terms of the following 3 criterions.

Criteria

○: The coating is transparent and has a smooth surface.

Δ: The coating is transparent but has a rough surface.

X: The coating is opaque and has a rough surface.

The coating was peeled off from the glass plate, thereby obtaining a film. The obtained film was subjected to the following measurements.

(1) Strength of a film was measured by TENSILON tensile strength tester (RTA-100, manufactured and sold by ORIENTEC CORPORATION, Japan), under the following conditions: length of a sample film: 300 mm; and tensile velocity: 50 mm/min.

(2) Solvent resistance of a film to a solvent was evaluated as follows. A film was disposed in a bag made of a 200-mesh metal wire net, and immersed in tetrahydrofuran and allowed to stand at room temperature for 24 hours. Subsequently, the weight retentivity of the film was calculated by the following formula:

(Weight of a film after being immersed in tetrahydrofuran)÷(Weight of a film before being immersed in tetrahydrofuran)×100.

(3) Water resistance of a film was evaluated as follows. A film was immersed in water and allowed to stand at room temperature for 6 days. Subsequently, the condition of the film was evaluated by visual observation, and the water absorption of the film was calculated by the following formula:

[(Weight of a film after being immersed in water)−(Weight of a film before being immersed in water)]÷(Weight of a film before being immersed in water)×100.

(4) Strength retentivity of a film was evaluated as follows. The tensile strength of a film at break and the tensile strength of the film at a tensile elongation of 100% were measured. Then, the film was immersed in water and allowed to stand at room temperature for 24 hours. Subsequently, the tensile strength of the film at break and the tensile strength of the film at a tensile elongation of 100% were measured. The retentivity of both of the tensile strength at break and the tensile strength at a tensile elongation of 100% were measured by the following formula:

(The value obtained after the film was immersed in water)÷(The value obtained before the film was immersed in water)×100.

REFERENTIAL EXAMPLE 1

Preparation of Aqueous Emulsions of Polycarbonyl Compounds (γ)

[Aqueous emulsion (1)]

220 Parts of deionized water and 2.3 parts of a 40% aqueous solution of sodium dioctylsulfosuccinate (Pelex® OTP: manufactured and sold by Kao Corp., Japan) were charged in a reactor having a reflux condenser, dropping tanks, a thermometer and a stirrer. After elevating the temperature in the reactor to 80° C., a liquid mixture of 9 parts of methacrylic acid, 4.5 parts of styrene, 234 parts of butyl acrylate, 13.5 parts of diacetoneacrylamide, 189 parts of methyl methacrylate, 230 parts of deionized water, 9 parts of Pelex OTP, 10 parts of a 25% aqueous solution of polyoxyethylene nonylphenyl ether (Emulgen®950: manufactured and sold by Kao Corp., Japan) and 1.0 part of ammonium persulfate was dropped into the reactor from the dropping tank over 3 hours. During the dropping of the above-mentioned liquid mixture into the reactor, the temperature in the reactor was maintained at 80° C. After completion of the dropping of the liquid mixture into the reactor, the mixture was allowed to stand for 2 hours while maintaining the temperature in the reactor at 80° C. After cooling the mixture in the reactor to room temperature, a 25% aqueous solution of ammonia was added to the mixture in the reactor to thereby adjust the pH value thereof to 8. Then, the resultant mixture was filtered by means of a 100-mesh metal wire net to thereby obtain an aqueous, carbonyl group-containing copolymer emulsion (1). With respect to the obtained emulsion, the solids content was 46.8%, and the average particle diameter of the dispersed phase was 1050 Å.

[Aqueous emulsion (2)]218 Parts of deionized water and 3.7 parts of a 25% aqueous solution of Adeca Rea® soap SE-1025N (manufactured and sold by Asahi Denka Kogyo K.K., Japan) were charged in a reactor having a reflux condenser, dropping tanks, a thermometer and a stirrer. After elevating the temperature in the reactor to 80° C., a liquid mixture of 9 parts of methacrylic acid, 4.5 parts of styrene, 234 parts of butyl acrylate, 13.5 parts of diacetoneacrylamide, 189 parts of methyl methacrylate, 225 parts of deionized water, 14.4 parts of Adeca Rea® soap SE-1025N, 8 parts of a 25% aqueous solution of polyoxyethylene nonylphenyl ether (Emulgen® 950: manufactured and sold by Kao Corp., Japan) and 1.0 part of ammonium persulfate was dropped into the reactor from the dropping tank over 3 hours. During the dropping of the above-mentioned liquid mixture into the reactor, the temperature in the reactor was maintained at 80° C. After completion of the dropping of the liquid mixture into the reactor, the mixture was allowed to stand for 2 hours while maintaining the temperature in the reactor at 80° C. After cooling the mixture in the reactor to room temperature, a 25% aqueous solution of ammonia was added to the mixture in the reactor to thereby adjust the pH value thereof to 8. Then, the resultant mixture was filtered by means of a 100-mesh metal wire net to thereby obtain an aqueous, carbonyl group-containing copolymer emulsion (2). With respect to the obtained emulsion, the solids content was 46.8%, and the average particle diameter of the dispersed phase was 1060 Å.

REFERENTIAL EXAMPLE 2

[Preparation of polyisocyanates]
[Polyisocyanate (1)]

222 Parts of isophorone diisocyanate (IPDI) represented by formula (13) shown below, 168 parts of hexamethylene diisocyanate and 2.4 parts of water as a biuretizing agent were dissolved in 130 parts of a mixed solvent of ethylene glycol methyl ether acetate and trimethyl phosphate (weight ratio 1:1) and reacted at 160° C. for 1.5 hours, thereby obtaining a reaction solution.

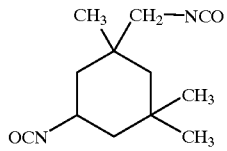

(13)

Using a wiped film evaporator (type 2-03 WFE, manufactured and sold by Shinko Pantec Co., Ltd., Japan), the obtained reaction solution was subjected to two-step distillation, comprising step (1) which was conducted at 160° C. under a pressure of 1.0 mmHg and step (2) which was conducted at 200° C. under a pressure of 0.1 mmHg, to thereby remove and recover unreacted isophorone diisocyanate and hexamethylene diisocyanate, and the solvent, thereby obtaining a residue.

The obtained residue contained 99.2 wt % of polyisocyanate (1) (a cobiuret-type polyisocyanate derived from isophorone diisocyanate and hexamethylene diisocyanate), 0.7 wt % of unreacted isophorone diisocyanate, and 0.1 wt % of unreacted hexamethylene diisocyanate. Further, the residue had an NCO group content of 15.6 wt %, a viscosity of 20,000 (+3,000)mPa.sec/40°, a number average molecular weight of about 800 (±100) and an average number of an NCO group of about 3.7. Ethyl acetate was added to the residue, thereby obtaining a 79.6% solution of polyisocyanate (1).

[Polyisocyanate (2)]

168 Parts of hexamethylene diisocyanate and 1.5 parts of water as a biuretizing agent were dissolved in 130 parts of a mixed solvent of ethylene glycol methyl ether acetate and trimethyl phosphate (weight ratio 1:1) and reacted at 160° C. for 1 hour, thereby obtaining a reaction solution. Using a wiped film evaporator (type 2-03 WFE, manufactured and sold by Shinko Pantec Co., Ltd., Japan), the obtained reaction solution was subjected to two-step distillation, comprising step (1) which was conducted at 160° C. under a pressure of 1.0 mmHg and step (2) which was conducted at 160° C. under a pressure of 0.1 mmHg, to thereby remove and recover unreacted hexamethylene diisocyanate and the solvent, thereby obtaining a residue.

The obtained residue contained 99.9 wt % of polyisocyanate (2) (a biuret-type polyisocyanate derived from hexamethylene diisocyanate) and 0.1 wt % of unreacted hexamethylene diisocyanate. Further, the residue had an NCO group content of 23.3 wt %, a viscosity of 1,900 (±200) mPa·sec/25°, a number average molecular weight of about 600 (±100) and an average number of NCO groups of about 3.3.

[Polyisocyanate (3)]

0.01 Part of tetramethyl ammonium acetate as an isocyanurate-forming catalyst was added to 1,000 parts of hexamethylene diisocyanate and reacted at 60° C. for 4 hours, thereby obtaining a reaction solution. Then, 0.2 part of phosphoric acid was added to the obtained solution, thereby terminating the reaction. The resultant reaction solution was further heated at 90° C. for 1 hour and then cooled to room temperature, thereby obtaining a solid deactivated catalyst as a precipitate. The precipitate was filtered off. Then, using a wiped film evaporator (type 2-03 WFE, manufactured and sold by Shinko Pantec Co., Ltd., Japan), the resultant reaction solution was subjected to two-step distillation, comprising step (1) which was conducted at 160° C. under a pressure of 1.0 mmHg and step (2) which was conducted at 160° C. under a pressure of 0.1 mmHg, to thereby remove and recover unreacted hexamethylene diisocyanate and the solvent, thereby obtaining a residue.

The obtained residue contained 99.9 wt % of polyisocyanate (3) (a isocyanurate-type polyisocyanate derived from hexamethylene diisocyanate) and 0.1 wt % of unreacted hexamethylene diisocyanate. Further, the residue had an NCO group content of about 23.4 wt %, a viscosity of 1400 (±200)mPa.sec/25°, a number average molecular weight of about 580 (±80) and an average number of NCO groups of about 3.2.

EXAMPLE 1

23 Parts of acetone, 23 parts of a solution of polyisocyanate (1) prepared in Referential Example 2 [a 79.6% solution of polyisocyanate (1) in ethyl acetate, having an NCO group content of 15.6 wt %], 10 parts of "Uniox® M1000" (polyoxyethylene methyl ether having a hydroxyl value: 56.9) (manufactured and sold by Nippon Oil & Fats Co., Ltd., Japan), and 0.001 part of dibutyltin dilaurate as a catalyst, were charged in a reactor having a reflux condenser, a thermometer and a stirrer, and reacted at 60° C. for 4 hours to thereby obtain a reaction mixture (i). On the other hand, 421 parts of acetone were charged in another reactor having a reflux condenser, a thermometer and a stirrer. 74 Parts of hydrazine monohydrate were added to the reactor over 30 minutes at room temperature while stirring, followed by further stirring for 1 hour, to thereby obtain a reaction mixture (ii). The reaction mixture (i) was added to the reaction mixture (ii) over 1 hour at 40° C. while stirring, followed by further stirring at 40° C. for 4 hours. To the resultant reaction mixture were added 1,183 parts of water over 30 minutes at 40° C. while stirring, followed by further stirring for 30 minutes. The resultant reaction mixture was subjected to distillation under heating and evacuation, to thereby remove acetone, ethyl acetate, hydrazine, a reaction product of acetone with hydrazine, and water, thereby obtaining an aqueous dispersion of a semicarbazide composition. With respect to the obtained dispersion, the solids content was 25%.

The infrared absorption spectrum of the dispersion is shown in FIG. 1.

100 Parts of cyclohexanone were added to 50 parts of the obtained aqueous dispersion (solids content: 10 parts) of a semicarbazide composition. The resultant mixture was subjected to shaking at 150 rpm for 5 hours, followed by centrifugation at 10,000 rpm for 10 minutes, to thereby separate the dispersion into an upper layer comprising a cyclohexanone phase and a lower layer comprising an aqueous phase. As a result, it was found that, the upper layer (cyclohexanone phase) contained 3.3 parts of semicarbazide derivatives and terminal-blocked forms thereof, derived from polyisocyanate (1), and the lower layer (aqueous phase) contained 6.7 parts of hydrophilic group-containing compounds and terminal-blocked forms thereof, derived from polyisocyanate (1), which compounds and terminal-blocked form thereof have, as a hydrophilic group, a polyoxyethylene methyl ether group introduced thereto.

EXAMPLE 2

22 Parts of tetrahydrofuran, 23 parts of a solution of polyisocyanate (1) prepared in Referential Example 2 [a 79.6% solution of polyisocyanate (1) in ethyl acetate, having an NCO group content of 15.6 wt %], 10 parts of "Uniox® M1000" (polyoxyethylene methyl ether having a hydroxyl value: 56.9) (manufactured and sold by Nippon Oil & Fats Co., Ltd., Japan), and 0.001 part of dibutyltin dilaurate as a catalyst, were charged in a reactor having a reflux condenser, a thermometer and a stirrer, and reacted at 60° C. for 4 hours to thereby obtain a reaction mixture (i). On the other hand, 147 parts of tetrahydrofuran were charged in another reactor having a reflux condenser, a thermometer and a stirrer. 7.3 Parts of hydrazine monohydrate were added to the reactor over 30 minutes at room temperature while stirring, followed by further stirring for 1 hour, to thereby obtain a mixture (ii). The reaction mixture (i) was added to the mixture (ii) over 1 hour at 40° C. while stirring, followed by further stirring at 40° C. for 4 hours. To the resultant reaction mixture were added 182 parts of water over 30 minutes at 40° C. while stirring, followed by further stirring for 30 minutes. The resultant reaction mixture was subjected to distillation under heating and evacuation, to thereby remove tetrahydrofuran, ethyl acetate and water, thereby obtaining an aqueous dispersion of a semicarbazide composition. With respect to the obtained dispersion, the solids content was 30%.

Figure 2:
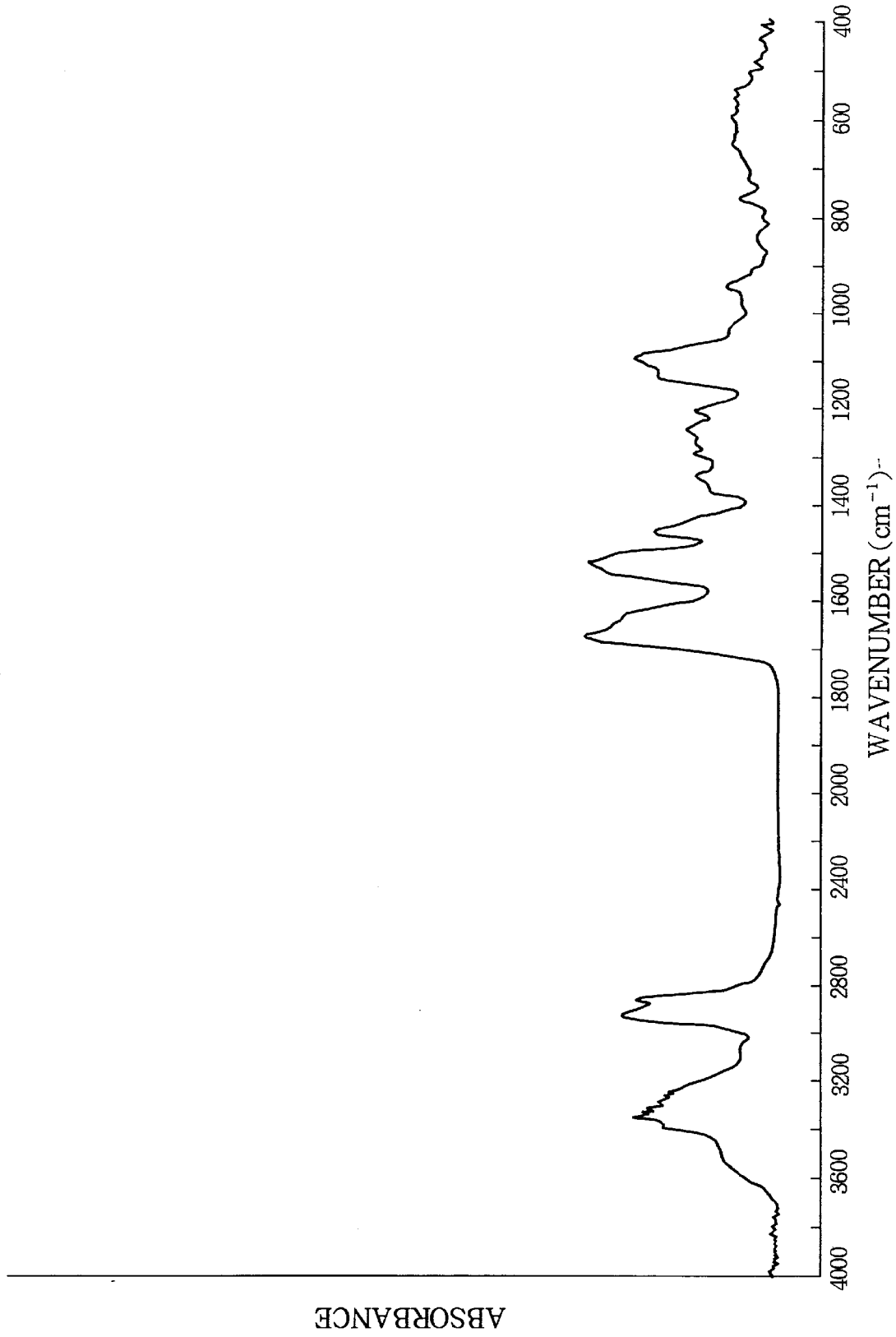
FIG. 2 shows an infrared absorption spectrum of the semicarbazide composition obtained in Example 2.

The infrared absorption spectrum of the dispersion is shown in FIG. 2.

EXAMPLE 3

259 Parts of acetone, 86 parts of isophorone diisocyanate (IPDI), 10 parts of "Uniox® M1000" (polyoxyethylene methyl ether having a hydroxyl value: 56.9) (manufactured and sold by Nippon Oil & Fats Co., Ltd., Japan), and 0.04 part of dibutyltin dilaurate as a catalyst, were charged in a reactor having a reflux condenser, a thermometer and a stirrer, and reacted at 60° C. for 7 hours to thereby obtain a reaction mixture (i). On the other hand, 2,600 parts of acetone were charged in another reactor having a reflux condenser, a thermometer and a stirrer. 459 Parts of hydrazine monohydrate were added to the reactor over 30 minutes at room temperature while stirring, followed by further stirring for 1 hour, to thereby obtain a reaction mixture (ii). The reaction mixture (i) was added to the reaction mixture (ii) over 1 hour at 40° C. while stirring, followed by further stirring at 40° C. for 4 hours. To the resultant reaction mixture were added, 4,100 parts of water over 30 minutes at 40° C. while stirring, followed by further stirring for 30 minutes. The resultant reaction mixture was subjected to distillation under heating and evacuation, to thereby remove acetone, hydrazine, a reaction product of acetone with hydrazine, and water, thereby obtaining an aqueous dispersion of hydrophilic group-containing compounds and terminal-blocked forms thereof, derived from IPDI. With respect to the obtained dispersion, the solids content was 40%.

Figure 3:
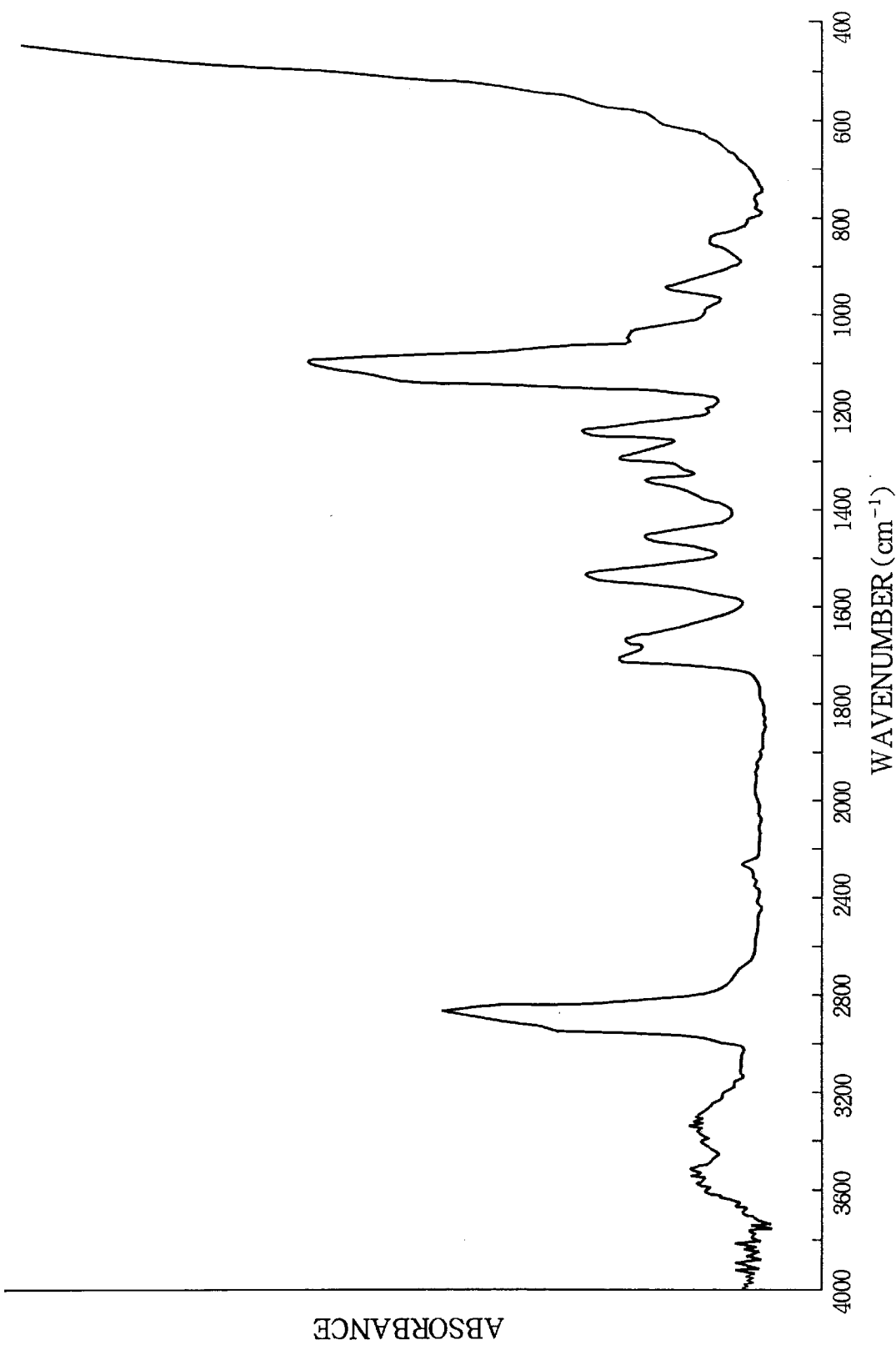
FIG. 3 shows an infrared absorption spectrum of the hydrophilic group-containing compound obtained in Example 3.

The infrared absorption spectrum of the dispersion is shown in FIG. 3.

597 Parts of hydrazine monohydrate were added to 3,390 parts of acetone at room temperature over 30 minutes while stirring, followed by further stirring for 1 hour. To the resultant reaction solution were added 161 parts of a solution of polyisocyanate (1) prepared in Referential Example 2 [a 79.6% solution of polyisocyanate (1) in ethyl acetate, having an NCO group content of 15.6 wt %] over 1 hour at 40° C. while stirring, followed by further stirring at 40° C. for 4 hours. To the resultant solution were added 180 parts of water over 30 minutes at 40° C. while stirring, followed by further stirring for 30 minutes. The resultant reaction mixture was subjected to distillation under heated and evaluated conditions, to thereby remove acetone, ethyl acetate, hydrazine, a reaction product of acetone with hydrazine, and water, thereby obtaining white crystals of semicarbazide derivatives and terminal-blocked forms thereof.

Figure 4:
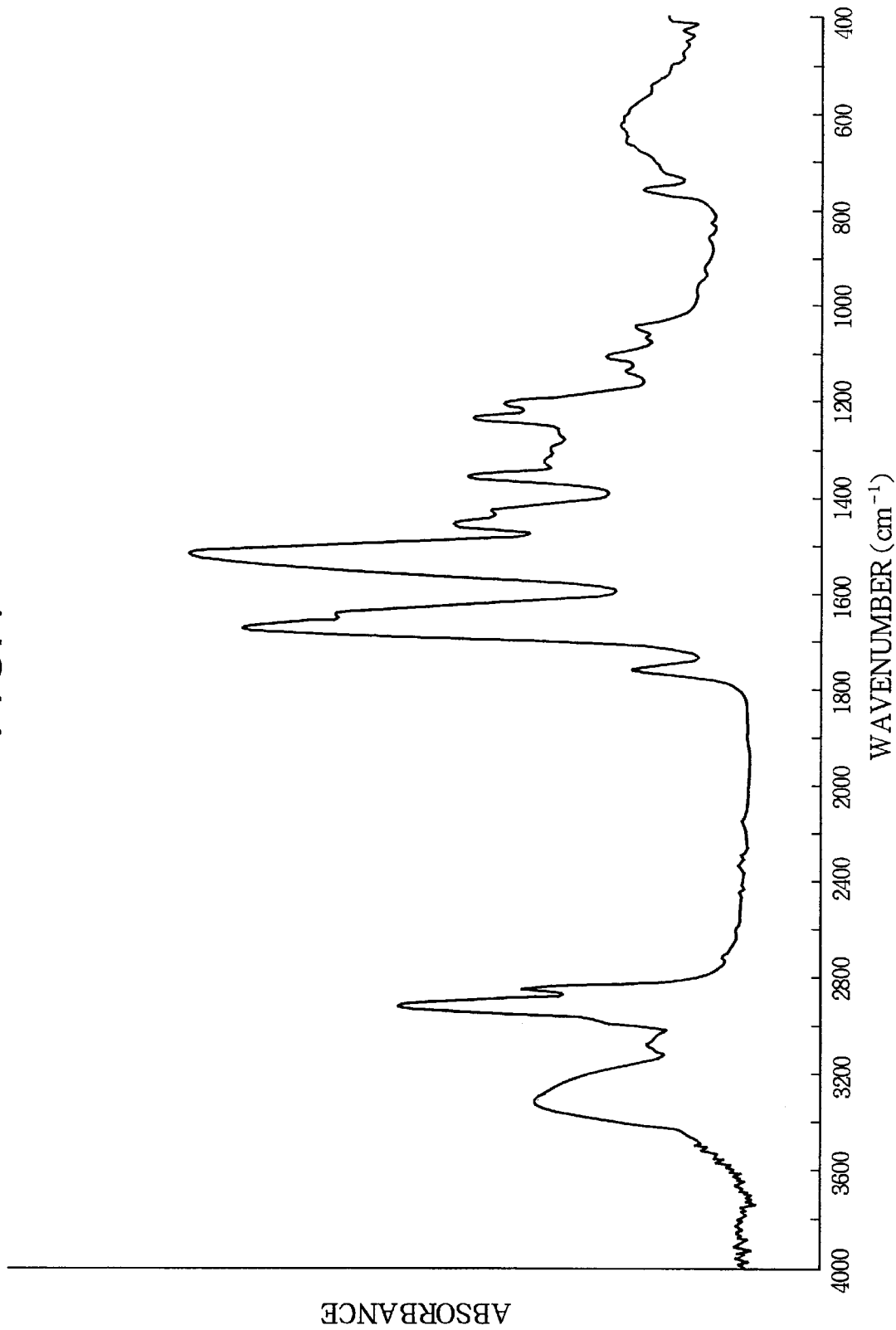
FIG. 4 shows an infrared absorption spectrum of the semicarbazide derivative obtained in Example 3.

The infrared absorption spectrum of the crystals is shown in FIG. 4.

To 80 parts of N-methylpyrrolidone were added 20 parts of the obtained semicarbazide derivatives and terminal-blocked forms thereof. To the resultant mixture were added 50 parts of the above-mentioned aqueous dispersion (solids content: 40%) of the hydrophilic group-containing compounds and terminal blocked forms thereof, derived from IPDI at room temperature while stirring, to thereby obtain a mixture. Subsequently, 50 parts of water were added to the obtained mixture at room temperature while stirring, thereby obtaining an aqueous dispersion of a semicarbazide composition. With respect to the obtained dispersion, the solids content was 20%.

EXAMPLE 4

3,600 Parts of methyl ethyl ketone were charged in a reactor having a reflux condenser, a thermometer and a stirrer. Then, 400 parts of hydrazine monohydrate were added to the reactor over about 30 minutes at room temperature while stirring, followed by further stirring at 40° C. for 1 hour, to thereby obtain a reaction mixture. To the obtained reaction mixture was added a solution of polyisocyanate (2), which solution is obtained by dissolving 144 parts of polyisocyanate compound (2) prepared in Referential Example 2 (an NCO group content of 23.3 wt %) in 144 parts of methyl ethyl ketone at 40° C. over about 1 hour, followed by further stirring at 40° C. for 3 hours. The resultant reaction mixture was subjected to distillation under heating and evacuation, to thereby remove methyl ethyl ketone, hydrazine, a reaction product of methyl ethyl ketone with hydrazine, and water, thereby obtaining 168 parts of semicarbazide derivatives and terminal blocked forms thereof, having a biuret structure. The obtained semicarbazide derivatives and terminal-blocked forms thereof were subjected to analysis by gel permeation chromatography. As a result, it was found that a compound represented by formula (14) and a terminal-blocked form thereof was present in an amount of 47% by area (in terms of the % by area of the chromatogram), based on the semicarbazide derivatives and terminal-blocked forms thereof:

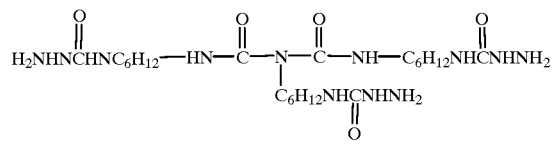

(14)

Figure 5:
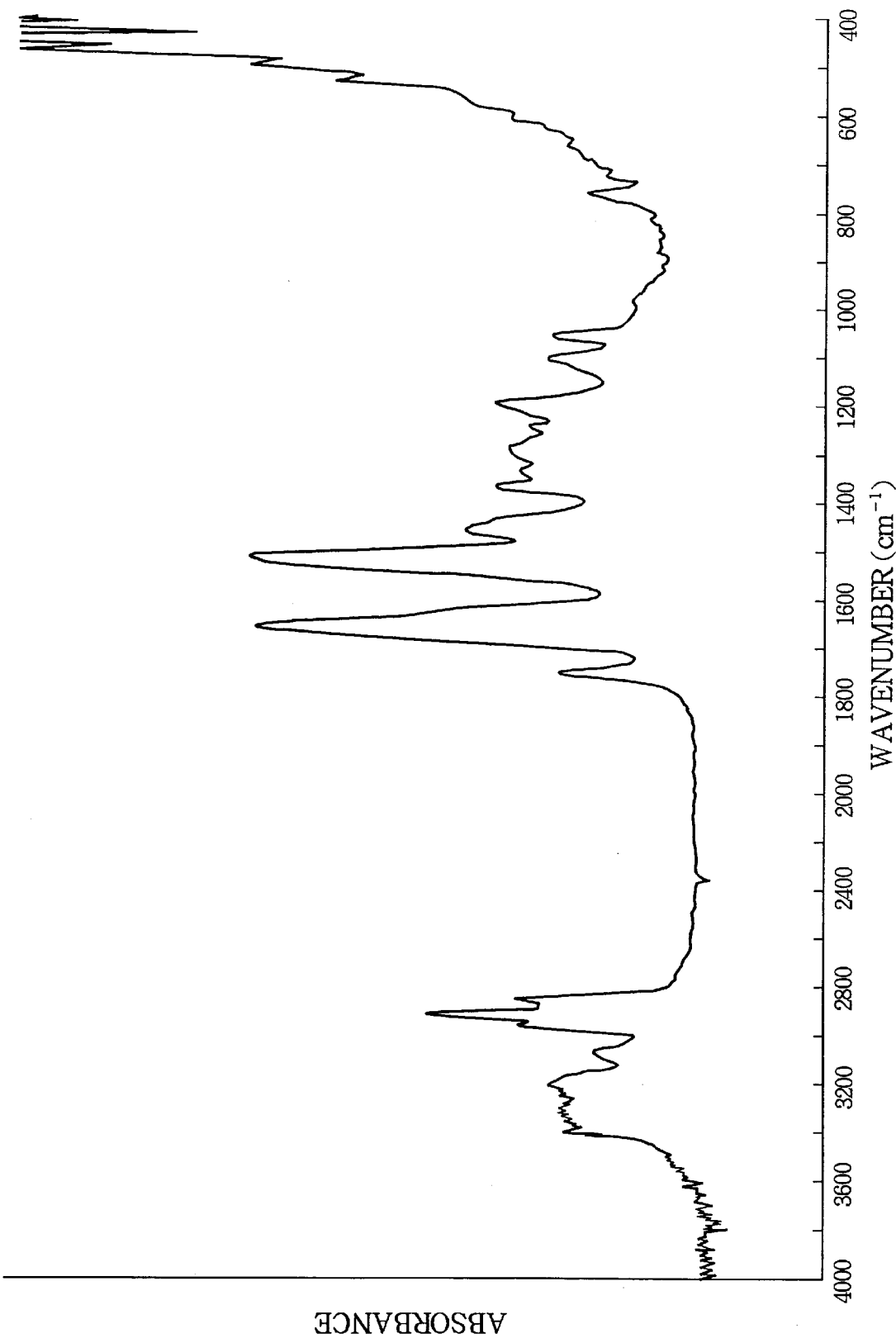
FIG. 5 shows an infrared absorption spectrum of the semicarbazide derivative obtained in Example 4.

The infrared absorption spectrum of the compound represented by formula (14) and a terminal blocked form thereof is shown in FIG. 5.

EXAMPLE 5

720 Parts of tetrahydrofuran were charged in a reactor having a reflux condenser, a thermometer and a stirrer, and 80 parts of hydrazine monohydrate were added to the reactor at room temperature. To the resultant mixture was added a solution of polyisocyanate (2), which solution obtained by dissolving 72 parts of polyisocyanate (2) prepared in Referential Example 2 (an NCO group content of 23.3 wt %) in 72 parts of tetrahydrofuran at 40° C. over about 1 hour, followed by further stirring at 40° C. for 3 hours. Subsequently, to the resultant mixture were added 360 parts of water over 30 minutes at 40° C. while stirring, and the reaction was allowed to continue for 30 minutes. The resultant reaction mixture was subjected to distillation under heating and evacuation, to thereby remove tetrahydrofuran, hydrazine and water, thereby obtaining an aqueous solution of semicarbazide derivatives having a biuret structure. With respect to the obtained solution, the solids content was 23%. The obtained semicarbazide derivatives were subjected to analysis by gel permeation chromatography. As a result, it was found that a compound represented by formula (14) was present in an amount of 57% by area (in terms of the % by area of the chromatogram), based on the semicarbazide derivatives:

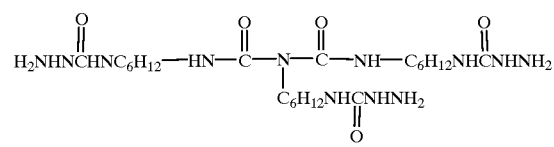

(14)

Figure 6:
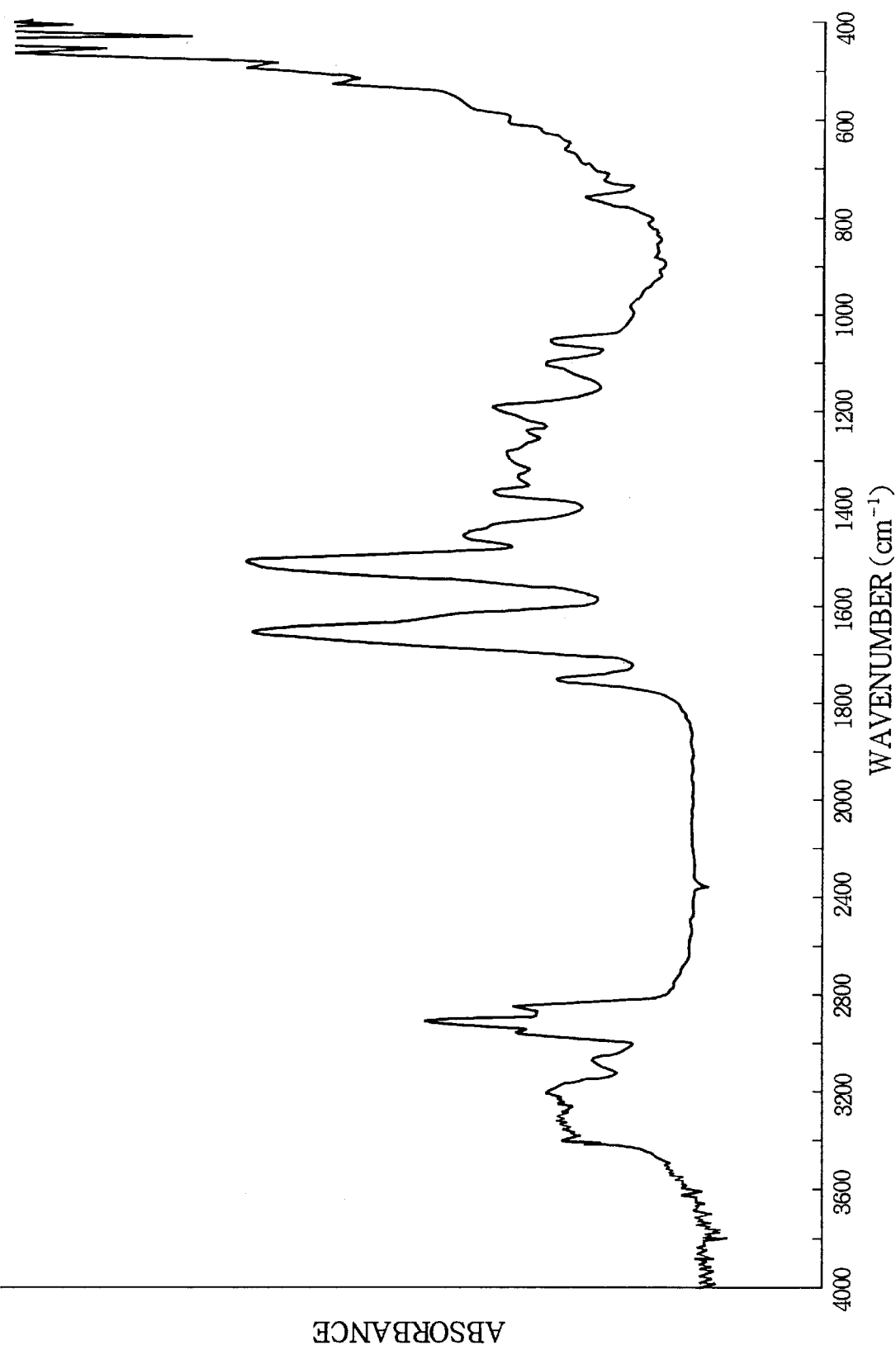
FIG. 6 shows an infrared absorption spectrum of the semicarbazide derivative obtained in Example 5.

The infrared absorption spectrum of the compound represented by formula (14) is shown in FIG. 6.

EXAMPLE 6

3,600 Parts of methyl ethyl ketone were charged in a reactor having a reflux condenser, a thermometer and a stirrer, and 400 parts of hydrazine monohydrate were added to the reactor over about 30 minutes at room temperature while stirring, followed by further stirring at 40° C. for 1 hour, to thereby obtain a reaction mixture. To the reaction mixture was added a solution of polyisocyanate (3), which solution was prepared by dissolving 73 parts of polyisocyanate (3) prepared in Referential Example 2 (an NCO group content of 23.1 wt %) in 73 parts of methyl ethyl ketone at 40 OC over about 30 minutes, followed by further stirring at 40° C. for 3 hours. The resultant reaction mixture was subjected to distillation under heating and evacuation, to thereby remove methyl ethyl ketone, hydrazine, a reaction product of methyl ethyl ketone with hydrazine, and water, thereby obtaining 84 parts of semicarbazide derivatives and terminal-blocked forms thereof, having isocyanurate structures. The obtained semicarbazide derivatives and terminal-blocked forms thereof were subjected to analysis by gel permeation chromatography. As a result, it was found that compound represented by formula (15) and a terminal-blocked form thereof were present in an amount of 58% by area (in terms of the % by area of the chromatogram), based on the semicarbazide derivatives and terminal-blocked forms thereof:

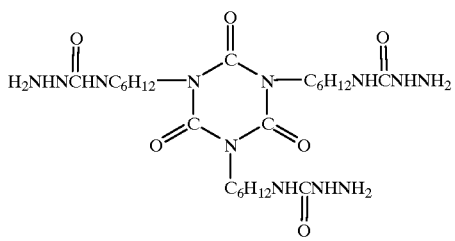

(15)

Figure 7:
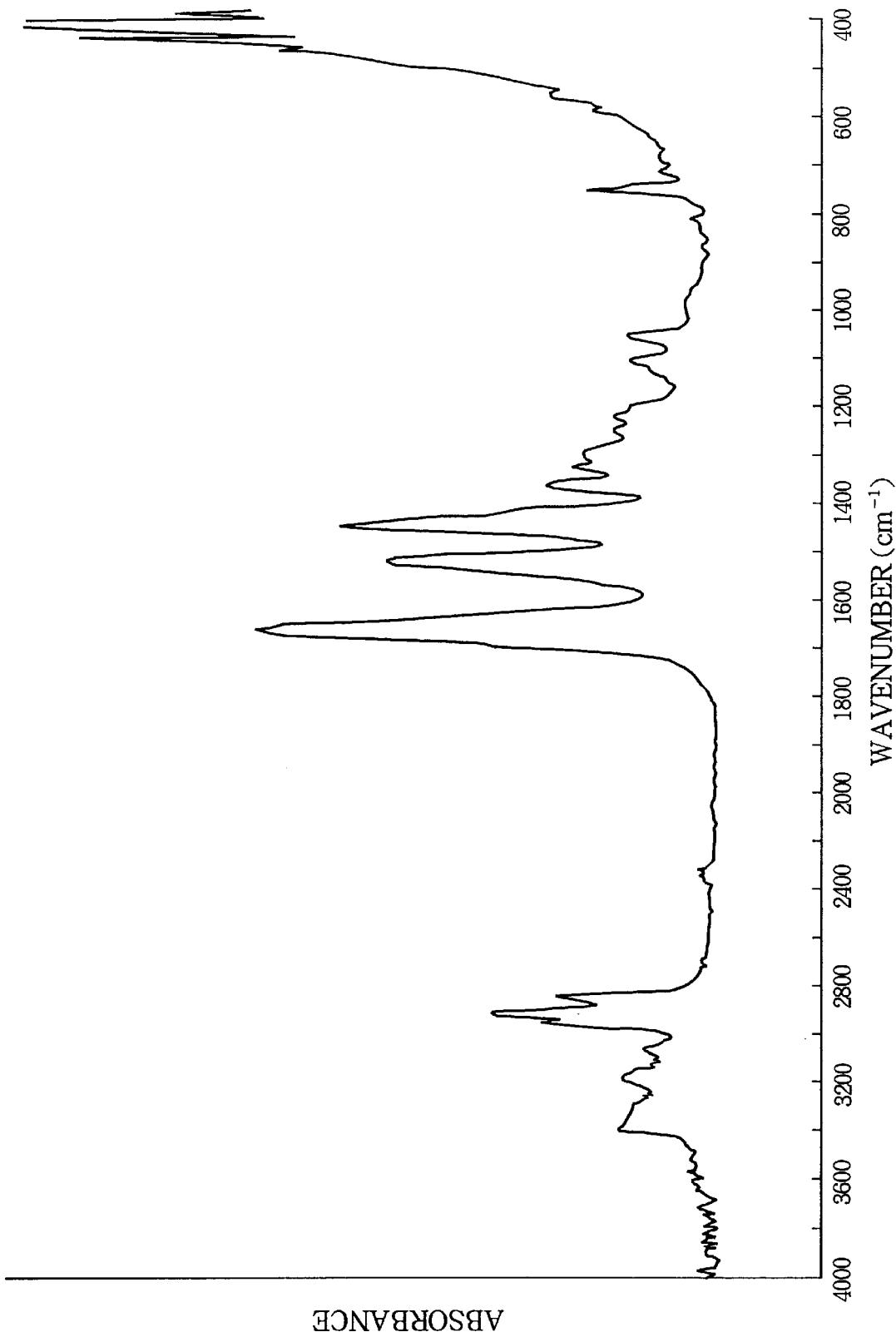
FIG. 7 shows an infrared absorption spectrum of the semicarbazide derivative obtained in Example 6.

The infrared absorption spectrum of the semicarbazide derivatives and terminal blocked forms thereof is shown in FIG. 7.

50 Parts of the obtained semicarbazide derivatives and terminal-blocked forms thereof were dissolved in 40 parts of toluene, thereby obtaining a mixture. To the obtained mixture were added 10 parts of GAFAC-RE610 (a specific phosphate-type nonionic anion-activating agent) (manufactured and sold by Toho Chemical Industry Co., Ltd., Japan). The resultant mixture was vigorously stirred at 5,000 rpm by a homogenizer. Subsequently, 100 parts of deionized water were added to the mixture over 20 minutes, thereby obtaining an aqueous dispersion of semicarbazide derivatives and terminal-blocked forms thereof.

EXAMPLE 7

120 Parts of adipic acid bishydrazide were dissolved in 1180 parts of deionized water. Then, 37 parts of methyl ethyl ketone were added to the resultant solution over about 10 minutes at room temperature while stirring. To the solution was added a mixture of a solution obtained by dissolving 13 parts of the polyisocyanate (3) prepared in Referential Example 2 in 13 parts of toluene, and 2.5 parts of GAFAC-RE610 over about 20 minutes, while vigorously stirring at 5,000 rpm by a homogenizer to thereby obtain an aqueous dispersion of semicarbazide derivatives and terminal-blocked forms thereof.

Figure 8:
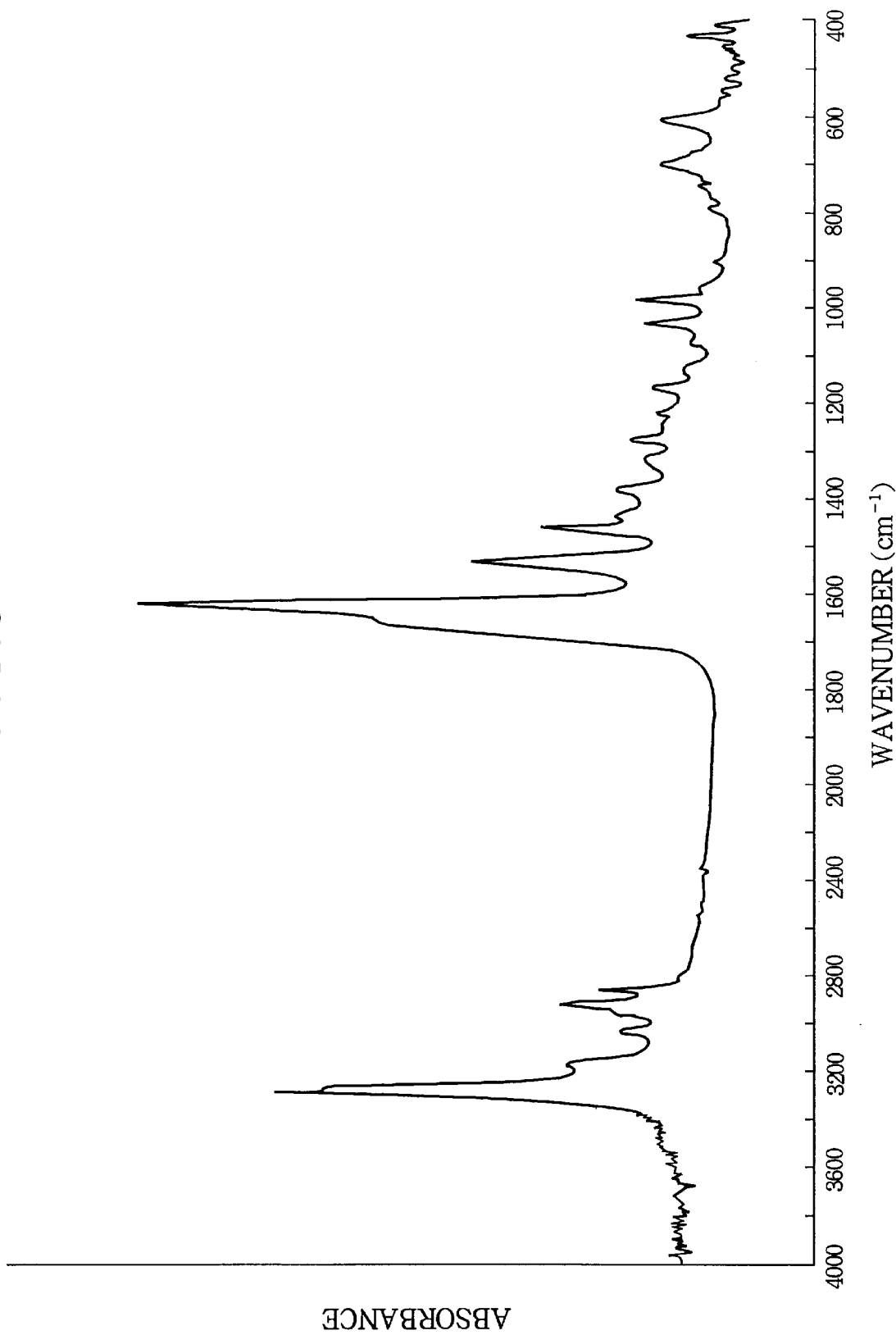
FIG. 8 shows an infrared absorption spectrum of the semicarbazide derivative obtained in Example 7.

The infrared absorption spectrum of the dispersion is shown in FIG. 8.

EXAMPLE 8

Hexamethylene diisocyanate was reacted with a triol (a number average molecular weight: 800) which was obtained by stepwise adding ε-caprolactone to trimethylol propane, in such an amount ratio that the resultant reaction mixture have the molar ratio of NCO group to OH group of 8. Then, unreacted hexamethylene diisocyanate was distilled off, to thereby obtain a triol-modified urethane type oligomer (NCO group content: 8.0 wt %) of hexamethylene diisocyanate.

1200 Parts of methyl ethyl ketone were charged in a reactor equipped with a reflux condenser, a thermometer and a stirrer, and 133 parts of hydrazine monohydrate were added to the reactor over 30 minutes at room temperature while stirring, followed by further stirring at 40° C. for 1 hour, to thereby obtain a reaction mixture (i). On the other hand, 140 parts of the above-mentioned triol-modified urethane type oligomer of hexamethylene diisocyanate were dissolved in a mixture of 15 parts of toluene and 124 parts of methyl ethyl ketone, to thereby obtain a reaction mixture (ii). The reaction mixture (i) was added to the reaction mixture (ii) over 1 hour at 40° C. while stirring, followed by further stirring for 3 hours at 40° C. The resultant reaction mixture was subjected to distillation under heating and evacuation, to thereby remove methyl ethyl ketone, hydrazine, toluene, a reaction product of methyl ethyl ketone with hydrazine, and water, thereby obtaining 147 parts of semicarbazide derivatives and terminal-blocked forms thereof having a urethane structure.

Figure 9:
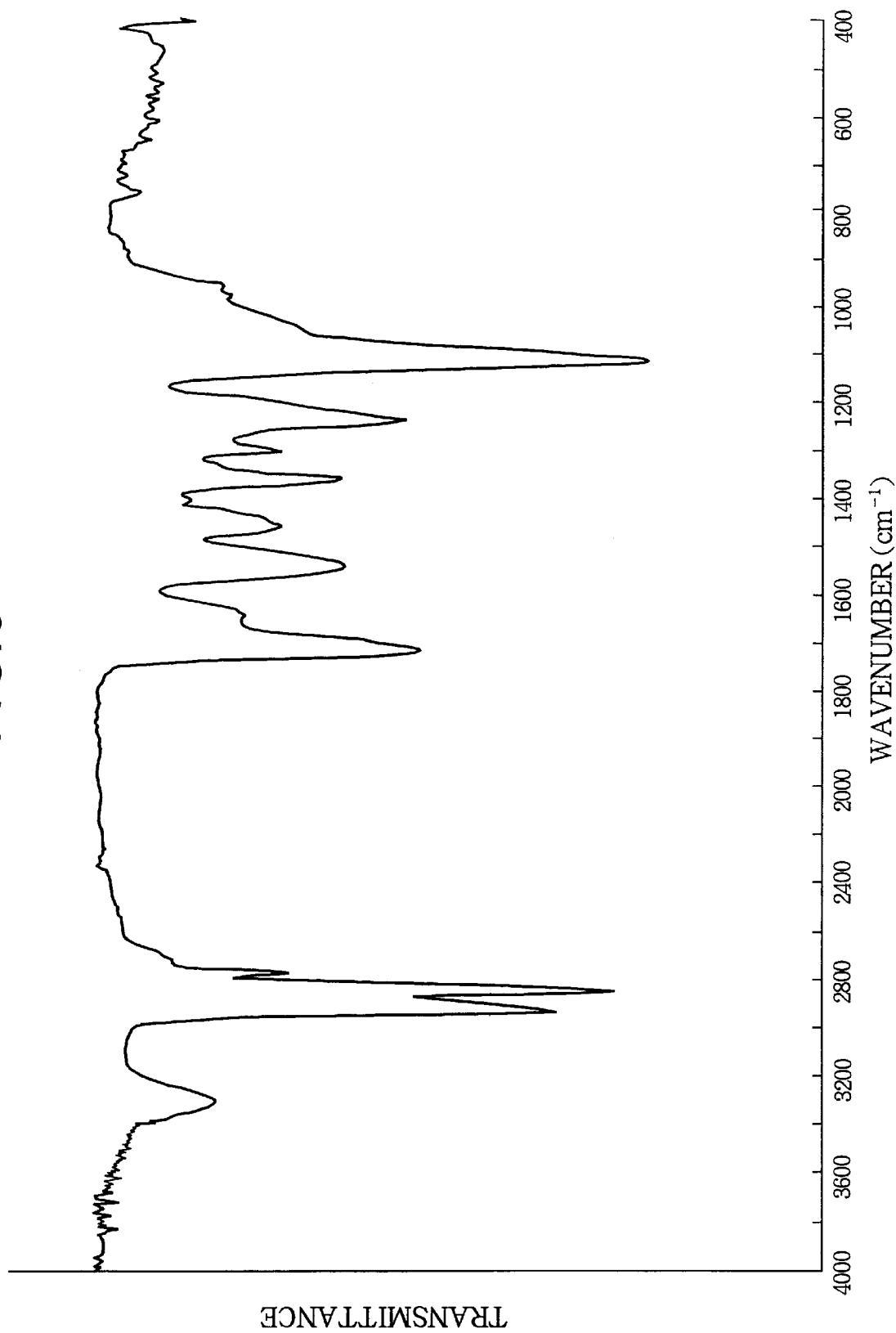
FIG. 9 shows an infrared absorption spectrum of the semicarbazide derivative obtained in Example 8.

The infrared absorption spectrum of the semicarbazide derivatives and terminal-blocked forms thereof is shown in FIG. 9.

EXAMPLE 9

13.2 Parts of the aqueous dispersion of the semicarbazide composition obtained in Example 1 were added to 100 parts of the aqueous, carbonyl group-containing copolymer emulsion (1) prepared in Referential Example 1, followed by stirring at room temperature for 30 minutes to thereby obtain a coating composition. The obtained coating composition was coated on a glass plate and dried at room temperature. The coating formed on the glass plate was further dried for 1 month at room temperature, thereby obtaining a transparent coating having a smooth surface.

Various properties of the coating were measured in accordance with the above-mentioned methods. Results are shown in Table 1.

EXAMPLE 10

13.2 Parts of the aqueous dispersion of the semicarbazide composition obtained in Example 1 were added to 100 parts of the aqueous, carbonyl group-containing copolymer emulsion (2) prepared in Referential Example 1, followed by stirring at room temperature for 30 minutes to thereby obtain a coating composition. The obtained coating composition was coated on a glass plate and dried at room temperature. The coating formed on the glass plate was further dried for 1 month at room temperature, thereby obtaining a transparent coating having a smooth surface.

Various properties of the coating were measured in accordance with the above-mentioned methods. Results are shown in Table 1.

EXAMPLE 11

10.5 Parts of the aqueous dispersion of the semicarbazide composition obtained in Example 2 were added to 100 parts of the aqueous, carbonyl group-containing copolymer emulsion (2) prepared in Referential Example 1, followed by stirring at room temperature for 30 minutes to thereby obtain a coating composition. The obtained coating composition was coated on a glass plate and dried at room temperature. The coating formed on the glass plate was further dried for 1 month at room temperature, thereby obtaining a transparent coating having a smooth surface.

Various properties of the coating were measured in accordance with the above-mentioned methods. Results are shown in Table 1.

EXAMPLE 12

18.8 Parts of the aqueous dispersion of the semicarbazide composition obtained in Example 3 were added to 100 parts of the aqueous, carbonyl group-containing copolymer emulsion (1) prepared in Referential Example 1, followed by stirring at room temperature for 30 minutes to thereby obtain a coating composition. The obtained coating composition was coated on a glass plate and dried at room temperature. The coating formed on the glass plate was further dried for 1 month at room temperature, thereby obtaining a transparent coating having a smooth surface.

The obtained coating was peeled off from the glass plate, thereby obtaining a film. Then, various properties of the obtained film were measured in accordance with the above-mentioned methods. As a result, it was found that the film had a weight retention (a criterion for the evaluation of solvent resistance of a film) of 92%. Further, it was also found that the film had an excellent water resistance (i.e., the water absorption is of the film was as low as 5%, and the condition of the film did not change).

EXAMPLE 13

18.8 Parts of the aqueous dispersion of the semicarbazide composition obtained in Example 3 were added to 100 parts of the aqueous, carbonyl group-containing copolymer emulsion (2) prepared in Referential Example 1, followed by stirring at room temperature for 30 minutes to thereby obtain a coating composition. The obtained coating composition was coated on a glass plate and dried at room temperature. The coating formed on the glass plate was further dried for 1 month at room temperature, thereby obtaining a transparent coating having a smooth surface.

The obtained coating was peeled off from the glass plate, thereby obtaining a film. Then, various properties of the obtained film were measured in accordance with the above-mentioned methods. As a result, it was found that the film had a weight retention (a criterion for the evaluation of solvent resistance of a film) of 95%. Further, it was also found that the film had an excellent water resistance (i.e., the water absorption of the film was as low as 4%, and the condition of the film did not change).

COMPARATIVE EXAMPLE 1

A coating was obtained in substantially the same manner as in Example 9 except that the aqueous, carbonyl group-containing copolymer emulsion (1) prepared in Referential Example 1 was solely used.

Various properties of the coating were measured in accordance with the above-mentioned methods. Results are shown in Table 1.

COMPARATIVE EXAMPLE 2

A coating was obtained in substantially the same manner as in Example 9, except that 14.5 parts of 5% aqueous solution of adipic acid bishydrazide (manufactured and sold by Japan Hydrazine Co. Inc., Japan) were used instead of the aqueous dispersion of semicarbazide composition prepared in Example 1.

Various properties of the coating were measured in accordance with the above-mentioned methods. Results are shown in Table 1.

COMPARATIVE EXAMPLE 3

105.2 Parts of isopholon diisocyanate (IPDI), 308.7 parts of polytetramethylene glycol (weight average molecular weight: 2,000), 21.2 parts of dimethylol propionic acid, 16.0 parts of triethylamine, 452.7 parts of methyl ethyl ketone and 0.013 part of dibutyltin dilaurate were charged in a reactor having a reflux condenser, a thermometer and a stirrer, and urethanizing reaction was carried out for 5 hours under a nitrogen gas flow at 80° C., to thereby obtain a solution of a prepolymer having terminal NCO groups. 309 Parts of water were added to 290 parts of the obtained solution at 40° C. while stirring, and then 31.6 parts of 10% aqueous solution of hydrazine were added to the resultant solution, followed by further stirring at 40° C. for 4 hours. The resultant reaction mixture was subjected to distillation under heating and evacuation, to thereby remove methyl ethyl ketone. Then, the concentration of the mixture was adjusted using deionized water, thereby obtaining an aqueous dispersion of semicarbazide group-containing oligourethane. With respect to the obtained dispersion, the solids content was 30%. Results of the gel permeation chromatography show that the weight average molecular weight of the oligomer was 29,000.

Figure 10:
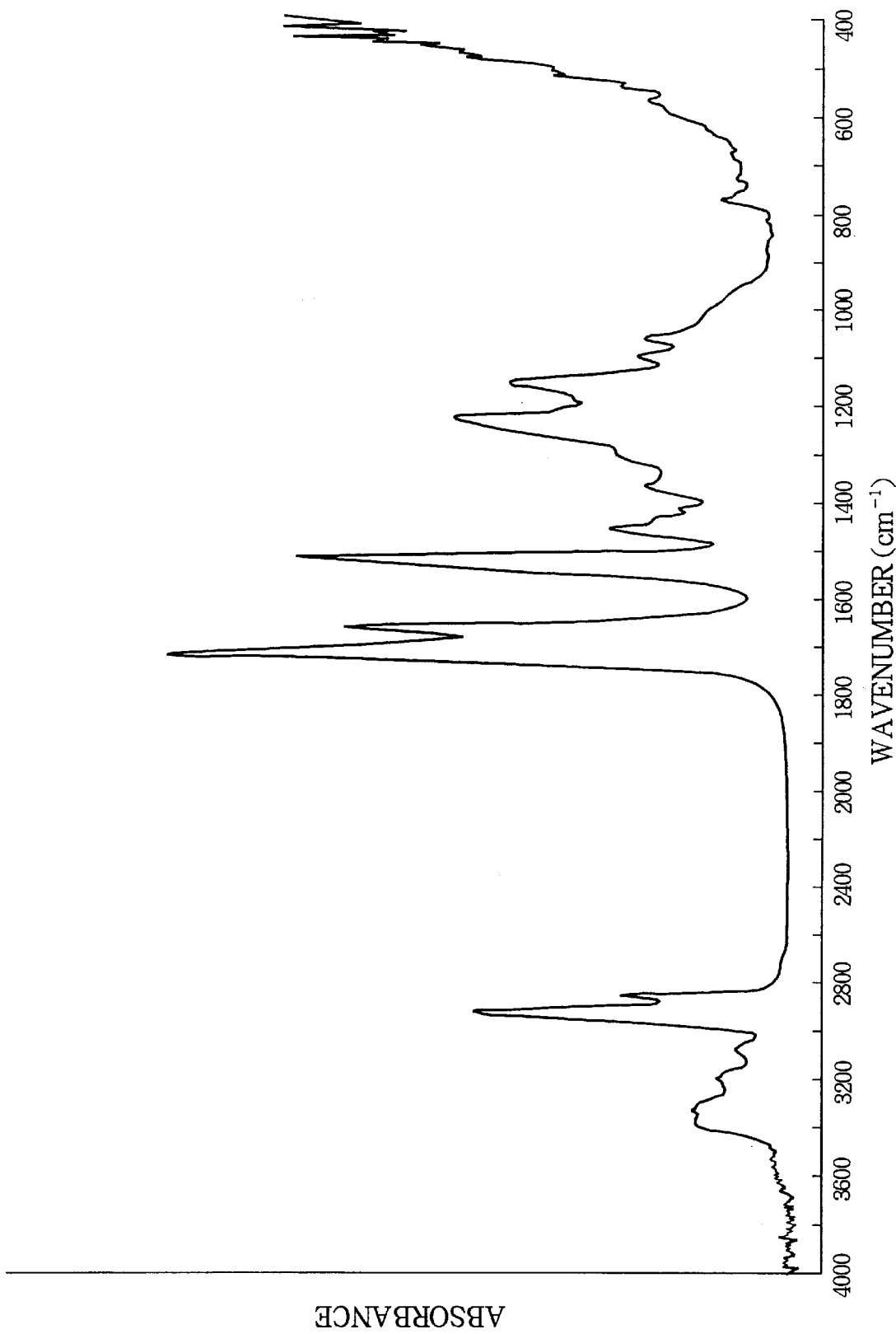
FIG. 10 shows an infrared absorption spectrum of the semicarbazide group-containing oligourethane obtained in Comparative Example 3.

The infrared absorption spectrum of the dispersion is shown in FIG. 10.

100 Parts of the above-mentioned aqueous dispersion of semicarbazide group-containing oligourethane were added to 100 parts of the aqueous, carbonyl group-containing copolymer emulsion (2) prepared in Referential Example 1, followed by stirring at room temperature for 30 minutes to thereby obtain a coating composition. The obtained coating composition was coated on a glass plate and dried at room temperature. The coating formed on the glass plate was further dried for 1 month at room temperature, thereby obtaining a transparent coating having a smooth surface.

Various properties of the coating were measured in accordance with the above-mentioned methods. Results are shown in Table 1.

COMPARATIVE EXAMPLE 4

40 Parts of hydrazine monohydrate were added to 360 parts of tetrahydrofuran in a reactor having a reflux condenser, a thermometer and a stirrer at room temperature over 30 minutes. Then, to the resultant solution was added a mixture of 16 parts of hexamethylene diisocyanate and 16 parts of tetrahydrofuran at room temperature over 1 hour, followed by further stirring for 24 hours. Then, 80 parts of water were added to the reaction solution while stirring over 30 minutes, followed by further stirring for 30 minutes. The obtained reaction solution was subjected to distillation under heating and evacuation to thereby remove tetrahydrofuran, hydrazine, and water, thereby obtaining an aqueous solution of semicarbazide derivatives. With respect to the obtained solution, the solids content was 30%.

3.2 Parts of the 30% aqueous solution of semicarbazide derivatives were added to 100 parts of the aqueous, carbonyl group-containing copolymer emulsion (1) prepared in Referential Example 1, followed by stirring at room temperature for 30 minutes to thereby obtain a coating composition. The obtained coating composition was coated on a glass plate and dried at room temperature. The coating formed on the glass plate was further dried for 1 month at room temperature, thereby obtaining a coating. Results are shown in Table 1.

TABLE 1

| | Example 9 | Comp. Example 1 | Comp. Example 2 | Comp. Example 3 | Comp. Example 4 | Example 10 | Example 11 |
|---|---|---|---|---|---|---|---|
| Thickness of film | 51 | 55 | 52 | 51 | 52 | 51 | 51 |
| Appearance of film | ○ | Δ | x | ○ | ○ | ○ | ○ |
| Tensile strength of film at break (kgf/cm$^2$) | 169 | 108 | 153 | 120 | 160 | 174 | 177 |
| Tensile strength of film at a tensile elongation of 100% (kgf/cm$^2$) | 45 | 21 | 59 | 25 | 58 | 55 | 61 |
| Water resistance | | | | | | | |
| Water absorption (%) | 2 | 34 | 53 | 30 | 35 | 1 | 1 |
| Condition of film | No change | Whitening | Whitening | Whitening | Whitening | No change | No change |
| Retentivity of tensile strength of film at break (%) | 80 | 55 | 43 | 45 | 56 | 95 | 97 |
| Retentivity of tensile strength of film at a tensile elongation of 100% (%) | 90 | 41 | 38 | 40 | 48 | 98 | 100 |
| Solvent resistance | | | | | | | |
| Weight retentivity (%) | 94 | 0 | 96 | 53 | 95 | 96 | 97 |

INDUSTRIAL APPLICABILITY

Each of (α) at least one member selected from the group consisting of the semicarbazide derivative and a terminal-blocked form thereof according to the present invention, and (δ) the semicarbazide composition of the present invention comprising at least one member selected from the group consisting of the semicarbazide derivative and a terminal-blocked form thereof and at least one member selected from the group consisting of a hydrophilic group-containing compound and a terminal-blocked form thereof, exhibits extremely high compatibility with a polycarbonyl compound, and excellent solubility in various solvents. When (α) at least one member selected from the group consisting of the semicarbazide derivative and a terminal-blocked form thereof according to the present invention or (δ) the semicarbazide composition of the present invention, is combined as a curing agent with a polycarbonyl compound to prepare a coating composition, the coating composition has not only excellent cold-curing ability and storage stability, but is also capable of forming, at relatively low temperatures (ambient temperature), a coating having an extremely high cross-linking degree and having various excellent properties including excellent hardness, toughness, water resistance and stain resistance, the coating being comparable to a coating obtained from a conventional organic solvent type coating material, especially in water resistance. Therefore, the coating composition of the present invention can be advantageously used as a paint, an undercoating or finish coating material for building materials, an adhesive, a pressure-sensitive adhesive, a processing agent for papers, or a finish coating material for textile fabrics.

What is claimed is:

1. A coating composition comprising (α) at least one member selected from the group consisting of a semicarbazide derivative represented by formula (1) and a terminal-blocked form thereof:

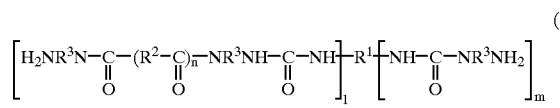

wherein R$^1$ represents a terminal isocyanate group-free polyisocyanate residue derived from a 3- to 20-mer oligomer of at least one diisocyanate selected from the group consisting of a linear or branched C$_2$–C$_{20}$ alkylene diisocyanate, a C$_5$–C$_{20}$ cycloalkylene diisocyanate which is unsubstituted or substituted with a C$_1$–C$_{18}$ alkyl group, a C$_1$–C$_8$ alkoxy group or a C$_1$–C$_6$ alkylene group, a C$_6$–C$_{20}$ arylene diisocyanate which is unsubstituted or substituted with a C$_1$–C$_{18}$ alkyl group or a C$_1$–C$_8$ alkoxy group, and a C$_8$–C$_{20}$ aralkylene diisocyanate which is unsubstituted or substituted with a C$_1$–C$_{18}$ alkyl group or a C$_1$–C$_8$ alkoxy group, or R$^1$ represents a terminal isocyanate group-free triisocyanate residue derived from a C$_2$–C$_{20}$ alkylene diisocyanate substituted with a C$_1$–C$_8$ isocyanatoalkyl group;

R$^2$ represents a linear or branched C$_2$–C$_{20}$ alkylene group, a C$_5$–C$_{20}$ cycloalkylene group, or a C$_6$–C$_{10}$ arylene group which is unsubstituted or substituted with a C$_1$–C$_{18}$ alkyl group or a C$_1$–C$_8$ alkoxy group;

each R$^3$ independently represents a hydrogen atom or a C$_1$–C$_{20}$ alkyl group;

n is zero or 1; and each of l and m is independently zero or a positive integer, provided that l and m satisfy the relationship 3≦(l+m)≦20, wherein said terminal-blocked form of the semicarbazide derivative represented by formula (1) has at least one blocked terminal group derived from the terminal group H$_2$NR$^3$N— in formula (1), said blocked terminal group being represented by the formula R$^9$R$^8$C=NR$^3$N—, wherein each of R$^8$ and R$^9$ independently represents a hydrogen atom, a linear or branched C$_1$–C$_{20}$ alkyl group, a C$_5$–C$_{20}$ cycloalkyl group, or a C$_6$–C$_{10}$ aryl group which is unsubstituted or substituted with a C$_1$–C$_{18}$ alkyl group or a C$_1$–C$_8$ alkoxy group, with the proviso that said R$^8$ and R$^9$ together optionally form a ring structure, and (γ) a polycarbonyl compound comprising at least one member selected from the group consisting of a carbonyl group-containing polyurethane, an acetoacetylated polyvinyl alcohol, an acetoacetylated hydroxyalkyl cellulose, and a carbonyl group-containing copolymler of 0.1 to 30% by weight of (a) a carbonyl group-containing ethylenically unsaturated monomer with 70 to 99.9% by weight of (b) an ethylenically unsaturated monomer copolymerizable with said monomer (a).

2. The coating composition according to claim 1, wherein the weight ratio of said component (α) to said component (γ) is from 0.1/99.9 to 90/10.

3. The coating composition according to claim 1, wherein said component (γ) is a carbonyl group-containing copolymer of 0.1 to 30% by weight of (a) the carbonyl group-containing ethylenically unsaturated monomer with 70 to 99.9% by weight of (b) the ethylenically unsaturated monomer copolymerizable with said monomer (a).

4. The coating composition according to claim 1, which is in the form of at least one member selected from the group consisting of a dispersion thereof in an aqueous medium and a solution thereof in an aqueous medium, wherein the total of components (α) and (γ) is within the range of from 0.1 to 70% by weight, based on the weight of said dispersion and/or said solution.

5. The coating composition according to claim 4, which is obtained by mixing said component (α) and said component (γ), wherein each of said component (α) and said component (γ) is in the form of at least one member selected from the group consisting of a dispersion thereof in an aqueous medium and a solution thereof in an aqueous medium.

6. The coating composition according to claim 5, wherein said component (γ) is a carbonyl group-containing copolymer of 0.1 to 30% by weight of (a) the carbonyl group-containing ethylenically unsaturated monomer with 70 to 99.9% by weight of (b) the ethylenically unsaturated monomer copolymerizable with said monomer (a).

7. The coating composition according to claim 6, wherein said carbonyl group-containing copolymer as component (γ) is one which is obtained by at least one method selected from the group consisting of a suspension polymerization, emulsion polymerization and solution polymerization of (a) the carbonyl group-containing ethylenically unsaturated monomer and (b) the ethylenically unsaturated monomer copolymerizable with said monomer (a).

8. The coating composition according to claim 7, wherein said carbonyl group-containing copolymer as component (γ) is in the form of a latex which is obtained by an emulsion polymerization of (a) the carbonyl group-containing ethylenically unsaturated monomer and (b) the ethylenically unsaturated monomer copolymerizable with said monomer (a).

9. The coating composition according to claim 7, wherein said carbonyl group-containing copolymer as component (γ) is one which is obtained by copolymerizing (a) the carbonyl group-containing ethylenically unsaturated monomer with (b) the ethylenically unsaturated monomer copolymerizable with said monomer (a) in the presence of (c) an emulsifier comprising at least one member selected from the group consisting of a sulfonic acid group-containing ethylenically unsaturated monomer and a sulfonate group-containing ethylenically unsaturated monomer.

10. The coating composition according to claim 1, which is a paint, an undercoating or finish coating material for building materials, an adhesive, a pressure-sensitive adhesive, a processing agent for papers, or a finish coating material for textile fabrics.

11. A coating composition comprising (δ) the composition comprising, as component (α), at least one member selected from the group consisting of the semicarbazide derivative and the terminal-blocked form thereof according to claim 1, and, as component (β), at least one member selected from the group consisting of a hydrophilic group-containing compound represented by formula (7) and a terminal-blocked form thereof:

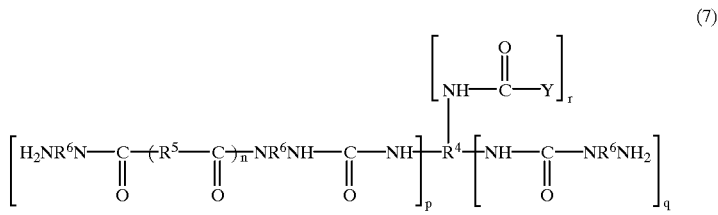

(7)

wherein $R^4$ represents a terminal isocyanate group-free polyisocyanate residue derived from a 3- to 20-mer oligomer of at least one diisocyanate selected from the group consisting of a linear or branched $C_2$–$C_{20}$ alkylene diisocyanate, a $C_5$–$C_{20}$ cycloalkylene diisocyanate which is unsubstituted or substituted with a $C_1$–$C_{18}$ alkyl group, a $C_1$–$C_8$ alkoxy group or a $C_1$–$C_6$ alkylene group, a $C_6$–$C_{20}$ arylene diisocyanate which is unsubstituted or substituted with a $C_1$–$C_{18}$ alkyl group or a $C_1$–$C_8$ alkoxy group, and a $C_8$–$C_{20}$ aralkylene diisocyanate which is unsubstituted or substituted with a $C_1$–$C_{18}$ alkyl group or a $C_1$–$C_8$ alkoxy group, or $R^4$ represents a terminal isocyanate group-free diisocyanate residue derived from said diisocyanate, or $R^4$ represents a terminal isocyanate group-free triisocyanate residue derived from a $C_2$–$C_{20}$ alkylene diisocyanate substituted with a $C_1$–$C_8$ isocyanatoalkyl group;

$R^5$ represents a linear or branched $C_2'$–$C_{20}$ alkylene group, a $C_5$–$C_{20}$ cycloalkylene group, or a $C_6$–$C_{10}$ arylene group which is unsubstituted or substituted with a $C_1$–$C_{18}$ alkyl group or a $C_1$–$C_8$ alkoxy group;

each $R^6$ independently represents a hydrogen atom or a $C_1$–$C_{20}$ alkyl group;

Y represents an organic group having at least one group selected from the group consisting of a nonionic hydrophilic group, an ionic hydrophilic group and a group which is capable of being converted into anionic hydrophilic group;

n is zero or 1; and each of p and q is independently zero or a positive integer, and r is a positive integer, provided that p and q satisfy the relationship $(p+q) \geq 0$, and p, q and r satisfy the relationship $2 \leq (p+q+r) \leq 20$, wherein said terminal-blocked form of said compound represented by formula (7) has at least one blocked terminal group derived from the terminal group $H_2NR^6N-$ in formula (7), said blocked terminal group being represented by the formula $R^9R^8C=NR^6N-$, wherein each of $R^8$ and $R^9$ independently represents a hydrogen atom, a linear or branched $C_1$–$C_{20}$ alkyl group, a $C_5$–$C_{20}$ cycloalyky group, or a $C_6$–$C_{10}$ aryl group which is unsubstituted or substituted with a $C_1$–$C_{18}$ alkyl group or a $C_1$–$C_8$ alkoxy group, with the proviso that said $R^8$ and $R^9$ together optionally form a ring structure, and wherein the weight ratio of said component (α) to said component (β) is 10/90 to 99/1, and (γ) a polycarbonyl compound comprising at least one member selected from the group consisting of a carbonyl group-containing polyurethane, an acetoacetylated polyvinyl alcohol, an acetoacetylated hydroxyalkyl cellulose, and a carbonyl group-containing copolymer of 0.1 to 30% by weight of (δ) a carbonyl group-containing ethylenically unsaturated monomer with 70 to 99.9% by weight of (b) an ethylenically unsaturated monomer copolymerizable with said monomer (a).

12. The coating composition according to claim 11, wherein the weight ratio of said component (δ) to said component (γ) is from 0.1/99.9 to 90/10.

13. The coating composition according to claim 11, wherein said component (γ) is a carbonyl group-containing copolymer of 0.1 to 30% by weight of (a) the carbonyl group-containing ethylenically unsaturated monomer with 70 to 99.9% by weight of (b) the ethylenically unsaturated monomer copolymerizable with said monomer (a).

14. The coating composition according to claim 11, which is in the form of at least one member selected from the group consisting of a dispersion thereof in an aqueous medium and a solution thereof in an aqueous medium, wherein the total of components (δ) and (γ) is within the range of from 0.1 to 70% by weight, based on the weight of said dispersion and/or said solution.

15. The coating composition according to claim 14, which is obtained by mixing said component (γ) and said component (γ), wherein each of said component (δ) and said component (γ) is in the form of at least one member selected from the group consisting of a dispersion thereof in an aqueous medium and a solution thereof in an aqueous medium.

16. The coating composition according to claim 15, wherein said component (r) is a carbonyl group-containing copolymer of 0.1 to 30% by weight of (a) the carbonyl group-containing ethylenically unsaturated monomer with 70 to 99.9% by weight of (b) the ethylenically unsaturated monomer copolymerizable with said monomer (a).

17. The coating composition according to claim 16, wherein said carbonyl group-containing copolymer as component (γ) is one which is obtained by at least one method selected from the group consisting of a suspension polymerization, emulsion polymerization and solution polymerization of (a) the carbonyl group-containing ethylenically unsaturated monomer and (b) the ethylenically unsaturated monomer copolymerizable with said monomer (a).

18. The coating composition according to claim 17, wherein said carbonyl group-containing copolymer as component (γ) is in the form of a latex which is obtained by an emulsion polymerization of (a) the carbonyl group-containing ethylenically unsaturated monomer and (b) the ethylenically unsaturated monomer copolymerizable with said monomer (a).

19. The coating composition according to claim 17, wherein said carbonyl group- containing copolymer as component (γ) is one which is obtained by copolymerizing (a) the carbonyl group-containing ethylenically unsaturated monomer with (b) the ethylenically unsaturated monomer copolymerizable with said monomer (a) in the presence of (c) an emulsifier comprising at least one member selected from the group consisting of a sulfonic acid group-containing ethylenically unsaturated monomer and a sulfonate group-containing ethylenically unsaturated monomer.

20. The coating composition according to claim 11, which is a paint, an undercoating or finish coating material for building materials, an adhesive, a pressure-sensitive adhesive, a processing agent for papers, or a finish coating material for textile fabrics.

* * * * *